(12) United States Patent
Pearcy et al.

(10) Patent No.: US 9,889,442 B2
(45) Date of Patent: *Feb. 13, 2018

(54) REAGENT PREPARATION AND DISPENSING DEVICE

(71) Applicant: Biolyph, L.L.C., Chaska, MN (US)

(72) Inventors: Timothy Pearcy, Plymouth, MN (US); James G. Skakoon, St. Paul, MN (US)

(73) Assignee: BIOLYPH, L.L.C., Chaska, MN (US)

(*) Notice: Subject to any disclaimer, the term of this patent is extended or adjusted under 35 U.S.C. 154(b) by 346 days.

This patent is subject to a terminal disclaimer.

(21) Appl. No.: 14/331,431

(22) Filed: Jul. 15, 2014

(65) Prior Publication Data
US 2014/0322102 A1    Oct. 30, 2014

Related U.S. Application Data

(63) Continuation of application No. 13/988,279, filed as application No. PCT/US2010/057238 on Nov. 18, 2010, now Pat. No. 8,919,390.

(51) Int. Cl.
*B01L 3/02*    (2006.01)
*A61M 5/28*    (2006.01)
(Continued)

(52) U.S. Cl.
CPC ........... *B01L 3/0206* (2013.01); *A61M 5/284* (2013.01); *A61M 5/31511* (2013.01); *B01L 3/52* (2013.01);
(Continued)

(58) Field of Classification Search
CPC ..... B01L 3/0206; B01L 3/52; A61M 5/31511; A61M 5/284; A61M 5/285;
(Continued)

(56) References Cited

U.S. PATENT DOCUMENTS 2,176,041 A    10/1939    Pittenger
2,591,706 A    4/1952    Lockhart
(Continued)

FOREIGN PATENT DOCUMENTS

AU    2011276396 B2    8/2014
AU    2014280969 A1    2/2015
(Continued)

OTHER PUBLICATIONS

US 8,807,178, 08/2014, Pearcy (withdrawn)
(Continued)

*Primary Examiner* — Nicolas A Arnett
(74) *Attorney, Agent, or Firm* — Schwegman Lundberg & Woessner, P.A.

(57) ABSTRACT

A reagent preparation and dispensing device includes a body having a reaction chamber for a reagent and a solution reservoir for a solution. The solution reservoir is isolated from the reaction chamber. A plunger is movably coupled with the body. Movement of the plunger from a starting position to a seated position pushes the solution into the reaction chamber. A dispensing path extends from the reaction chamber out of the body. The dispensing path is configured to dispense a reagent mixture formed from the solution and the reagent. A vent path extends from the reaction chamber, the vent path vents reaction chamber gas displaced by the addition of the solution to the reaction chamber throughout movement of the plunger from the starting position to the seated position.

34 Claims, 22 Drawing Sheets

(51) Int. Cl.
*A61M 5/315* (2006.01)
*B01L 3/00* (2006.01)
*A61M 5/31* (2006.01)
*A61M 5/178* (2006.01)

(52) U.S. Cl.
CPC ..... *A61M 5/285* (2013.01); *A61M 2005/1787* (2013.01); *A61M 2005/312* (2013.01); *A61M 2005/3104* (2013.01); *A61M 2005/3123* (2013.01)

(58) Field of Classification Search
CPC .... A61M 2005/312; A61M 2005/3104; A61M 2005/3123
USPC ....... 141/2, 4, 21, 25–27, 392; 422/501–514
See application file for complete search history.

(56) References Cited

U.S. PATENT DOCUMENTS

| | | | |
|---|---|---|---|
| 3,834,387 A | 9/1974 | Brown | |
| 4,031,892 A | 6/1977 | Hurschman | |
| 4,226,236 A | 10/1980 | Genese | |
| 4,515,753 A | 5/1985 | Smith et al. | |
| 4,516,967 A * | 5/1985 | Kopfer | A61J 1/2096 604/87 |
| 4,693,706 A | 9/1987 | Ennis, III et al. | |
| 4,768,568 A | 9/1988 | Fournier et al. | |
| 4,834,149 A | 5/1989 | Fournier et al. | |
| 4,973,168 A | 11/1990 | Chan | |
| 5,000,922 A | 3/1991 | Turpen | |
| 5,071,769 A | 12/1991 | Kundu et al. | |
| 5,199,949 A | 4/1993 | Haber et al. | |
| 5,232,664 A | 8/1993 | Krawzak et al. | |
| 5,277,873 A | 1/1994 | Hsei | |
| 5,281,198 A | 1/1994 | Haber et al. | |
| 5,449,494 A | 9/1995 | Seeney | |
| 5,605,542 A | 2/1997 | Tanaka et al. | |
| 5,637,087 A | 6/1997 | O'Neil et al. | |
| 5,704,918 A | 1/1998 | Higashikawa | |
| 5,785,682 A | 7/1998 | Grabenkort | |
| 5,827,262 A | 10/1998 | Neftel et al. | |
| 5,865,799 A | 2/1999 | Tanaka et al. | |
| 5,869,003 A | 2/1999 | Nason | |
| 5,879,635 A | 3/1999 | Nason | |
| 5,899,881 A | 5/1999 | Grimard et al. | |
| 5,951,160 A | 9/1999 | Ronk | |
| 5,965,453 A | 10/1999 | Skiffington et al. | |
| 5,971,953 A | 10/1999 | Bachynsky | |
| 6,045,755 A | 4/2000 | Lebl et al. | |
| 6,048,735 A | 4/2000 | Hessel et al. | |
| 6,248,294 B1 | 6/2001 | Nason | |
| 6,284,549 B1 | 9/2001 | Guthrie | |
| 6,406,175 B1 | 6/2002 | Marino | |
| 6,419,656 B1 | 7/2002 | Vetter et al. | |
| 6,481,435 B2 | 11/2002 | Hochrainer et al. | |
| 6,488,894 B1 | 12/2002 | Miethe et al. | |
| 6,551,834 B2 | 4/2003 | Carpenter et al. | |
| 6,569,125 B2 | 5/2003 | Jepson et al. | |
| 6,632,681 B1 | 10/2003 | Chu | |
| 6,641,561 B1 | 11/2003 | Hill et al. | |
| 6,656,150 B2 | 12/2003 | Hill et al. | |
| 6,702,778 B2 | 3/2004 | Hill et al. | |
| 6,770,052 B2 | 8/2004 | Hill et al. | |
| 6,817,987 B2 | 11/2004 | Vetter et al. | |
| 6,820,506 B2 * | 11/2004 | Kipke | B01F 5/0646 73/863 |
| 6,863,866 B2 | 3/2005 | Kelly et al. | |
| 6,878,338 B2 | 4/2005 | Taylor et al. | |
| 6,924,498 B2 | 8/2005 | Feldsine et al. | |
| 6,953,445 B2 | 10/2005 | Wilmot et al. | |
| 6,986,346 B2 * | 1/2006 | Hochrainer | A61K 9/0078 128/200.19 |
| 7,030,403 B2 | 4/2006 | Feldsine et al. | |
| 7,040,311 B2 | 5/2006 | Hochrainer et al. | |
| 7,090,803 B1 | 8/2006 | Gould et al. | |
| 7,329,235 B2 | 2/2008 | Bertron et al. | |
| 7,967,779 B2 | 6/2011 | Bertron et al. | |
| 8,329,119 B2 | 12/2012 | Pearcy et al. | |
| 8,919,390 B2 | 12/2014 | Pearcy et al. | |
| 8,940,539 B2 | 1/2015 | Pearcy et al. | |
| 8,973,749 B2 | 3/2015 | Pearcy et al. | |
| 2001/0016703 A1 | 8/2001 | Wironen et al. | |
| 2003/0039588 A1 | 2/2003 | Miethe et al. | |
| 2003/0157564 A1 | 8/2003 | Smith et al. | |
| 2003/0209653 A1 | 11/2003 | Feldsine et al. | |
| 2003/0235512 A1 | 12/2003 | Carpenter et al. | |
| 2004/0097874 A1 | 5/2004 | Griffiths et al. | |
| 2004/0138611 A1 | 7/2004 | Griffiths et al. | |
| 2004/0170533 A1 | 9/2004 | Chu | |
| 2005/0075602 A1 | 4/2005 | Cherif-cheikh et al. | |
| 2005/0075604 A1 * | 4/2005 | Lee | A61M 5/152 604/93.01 |
| 2006/0052747 A1 * | 3/2006 | Nishimura | A61M 5/288 604/85 |
| 2006/0079834 A1 | 4/2006 | Tennican et al. | |
| 2006/0116644 A1 | 6/2006 | Norton | |
| 2006/0139631 A1 | 6/2006 | Feldsine et al. | |
| 2006/0169348 A1 | 8/2006 | Yigal | |
| 2006/0184103 A1 | 8/2006 | Paproski et al. | |
| 2006/0216196 A1 | 9/2006 | Satoh et al. | |
| 2007/0014690 A1 | 1/2007 | Lawrence et al. | |
| 2008/0188799 A1 | 8/2008 | Mueller-Beckhaus et al. | |
| 2008/0188828 A1 | 8/2008 | Reynolds et al. | |
| 2008/0300551 A1 | 12/2008 | Schiller et al. | |
| 2009/0117646 A1 | 5/2009 | Stordeur et al. | |
| 2010/0249753 A1 | 9/2010 | Gaisser et al. | |
| 2011/0127294 A1 | 6/2011 | Pearcy et al. | |
| 2011/0224610 A1 | 9/2011 | Lum et al. | |
| 2011/0224611 A1 | 9/2011 | Lum et al. | |
| 2011/0224612 A1 | 9/2011 | Lum et al. | |
| 2012/0179137 A1 | 7/2012 | Bartlett et al. | |
| 2012/0201726 A1 | 8/2012 | Pearcy et al. | |
| 2013/0030412 A1 | 1/2013 | Bartlett et al. | |
| 2013/0208558 A1 | 8/2013 | Pearcy et al. | |
| 2014/0048556 A1 | 2/2014 | Pearcy et al. | |
| 2015/0125364 A1 | 5/2015 | Pearcy et al. | |

FOREIGN PATENT DOCUMENTS

| | | |
|---|---|---|
| AU | 2015202242 B2 | 11/2016 |
| CA | 2803375 C | 5/2016 |
| DE | 19543240 A1 | 5/1997 |
| EP | 1103304 A2 | 5/2001 |
| EP | 2405961 A2 | 1/2012 |
| EP | 2640526 B1 | 9/2016 |
| JP | 2006271938 A | 10/2006 |
| WO | WO-8603589 A1 | 6/1986 |
| WO | WO-9103224 A1 | 3/1991 |
| WO | WO-9210225 A1 | 6/1992 |
| WO | WO-9517916 A1 | 7/1995 |
| WO | WO-9630066 A1 | 10/1996 |
| WO | WO-9703209 A1 | 1/1997 |
| WO | WO-2009140502 A1 | 11/2009 |
| WO | WO-2010104858 A2 | 9/2010 |
| WO | WO-2011123762 A1 | 10/2011 |
| WO | WO-2012006185 A1 | 1/2012 |
| WO | WO-2012067619 A1 | 5/2012 |
| WO | WO-2013043861 A2 | 3/2013 |
| WO | WO-2013163598 A2 | 10/2013 |
| WO | WO-2014004695 A1 | 1/2014 |

OTHER PUBLICATIONS

"U.S. Appl. No. 12/992,552, Notice of Allowance dated Nov. 21, 2014", 7 pgs.

"U.S. Appl. No. 13/805,166, Notice of Allowability dated Jan. 23, 2015", 2 pgs.

"U.S. Appl. No. 13/988,279, Notice of Allowability dated Nov. 21, 2014", 2 pgs.

"U.S. Appl. No. 14/597,677, Appeal Brief filed Feb. 12, 2015", 6 pgs.

(56) References Cited

OTHER PUBLICATIONS

"Australian Application Serial No. 2010363976, First Examiners Report dated Jan. 7, 2015", 2 pgs.
"Australian Application Serial No. 2010363976, Response filed Apr. 16, 2015 to First Examiners Report dated Jan. 7, 2015", 3 pgs.
"Canadian Apllication Serial No. 2,803,375 Response filed Nov. 25, 2014 to Non Final Office Action dated Jun. 5, 2014", 1 Pg.
"U.S. Appl. No. 13/805,166, Notice of Allowance dated Oct. 15, 2014", 8 pgs.
"U.S. Appl. No. 13/805,166, Response filed Sep. 25, 2014 to Restriction Requirement dated Jul. 22, 2014", 14 pgs.
"U.S. Appl. No. 13/988,279, Notice of Allowance dated Aug. 22, 2014", 8 pgs.
"U.S. Appl. No. 13/805,166, Restriction Requirement dated Jul. 22, 2014", 8 pgs.
"Australian Application Serial No. 2011276396, Response filed Apr. 10, 2014 to Office Action dated Dec. 11, 2013", 19 pgs.
"U.S. Appl. No. 12/992,552, Examiner Interview Summary dated Jun. 11, 2013", 4 pgs.
"U.S. Appl. No. 12/992,552, Final Office Action dated Mar. 1, 2013", 21 pgs.
"U.S. Appl. No. 12/992,552, Non Final Office Action dated Aug. 2, 2012", 18 pgs.
"U.S. Appl. No. 12/992,552, Preliminary Amendment filed Nov. 12, 2010", 6 pgs.
"U.S. Appl. No. 12/992,552, Response filed Jul. 1, 2013 to Final Office Action dated Mar. 1, 2013", 23 pgs.
"U.S. Appl. No. 12/992,552, Response filed Dec. 20, 2012 to Non Final Office Action dated Aug. 2, 2012", 22 pgs.
"U.S. Appl. No. 12/992,552, Supplemental Preliminary Amendment filed Dec. 13, 2010", 9 pgs.
"U.S. Appl. No. 13/450,365, Notice of Allowance dated Aug. 16, 2012", 13 pgs.
"U.S. Appl. No. 13/450,365, Preliminary Amendment filed Jul. 27, 2012", 12 pgs.
"U.S. Appl. No. 13/805,166, Preliminary Amendment filed Dec. 18, 2012", 8 pgs.
"U.S. Appl. No. 13/988,279, Notice of Allowance dated Feb. 4, 2014", 9 pgs.
"U.S. Appl. No. 13/988,279, Notice of Allowance dated Apr. 1, 2014", 8 pgs.
"U.S. Appl. No. 13/988,279, Preliminary Amendment filed May 17, 2013", 9 pgs.
"U.S. Appl. No. 13/988,279, PTO Response to Rule 312 Communication dated Jun. 30, 2014", 2 pgs.
"Australian Application Serial No. 2009246306, Office Action dated Mar. 13, 2014", 4 pgs.
"Australian Application Serial No. 2009246306, Voluntary Amendment filed Jan. 25, 2011", 42 pgs.
"Australian Application Serial No. 2010363976, Amendment filed Apr. 29, 2014", 17 pgs.
"Australian Application Serial No. 2010363976, Office Action dated May 13, 2013", 2 pgs.
"Australian Application Serial No. 2010363976, Response filed May 22, 2013 to Office Action dated May 13, 2013", 58 pgs.
"Australian Application Serial No. 2011276396, First Examination Report dated Dec. 11, 2013", 3 pgs.
"Australian Application Serial No. 2011276396, Notice of Acceptance dated Apr. 24, 2014", 2 pgs.
"Australian Application Serial No. 2011276396, Voluntary Amendment filed Dec. 17, 2012", 14 pgs.
"Canadian Application Serial No. 2,803,375, Office Action dated Jun. 5, 2014", 2 pgs.
"European Application Serial No. 10859869.9, Extended European Search Report dated May 2, 2014", 7 pgs.
"European Application Serial No. 10859869.9, Office Action dated Jul. 5, 2013", 2 pgs.
"European Application Serial No. 10859869.9, Response filed Jul. 19, 2013 to Office Action dated Jul. 5, 2013", 54 pgs.

"European Application Serial No. 11804202.7, Extended European Search Report dated Jul. 7, 2014", 6 pgs.
"European Application Serial No. 11804202.7, Office Action dated Apr. 10, 2013", 2 pgs.
"International Application Serial No. PCT/US2010/057238, International Search Report dated Jan. 26, 2011", 2 pgs.
"International Application Serial No. PCT/US2010/057238, Written Opinion dated Jan. 26, 2011",9 pgs.
"International Application Serial No. PCT/US2009/043966, Demand and Response filed Mar. 12, 2010 to Written Opinion dated Jul. 31, 2009", 36 pgs.
"International Application Serial No. PCT/US2009/043966, International Preliminary Report on Patentability dated Jul. 27, 2011", 36 pgs.
"International Application Serial No. PCT/US2009/043966, Search Report dated Jul. 27, 2009", 7 pgs.
"International Application Serial No. PCT/US2009/043966, Written Opinion dated Jul. 27, 2009", 6 pgs.
"International Application Serial No. PCT/US2010/057238, Response to Written Opinion filed Sep. 18, 2012", 14 pgs.
"International Application Serial No. PCT/US2010/057238, International Preliminary Report on Patentability dated Dec. 14, 2012", 41 pgs.
"International Application Serial No. PCT/US2011/042443, International Preliminary Report on Patentability dated Jul. 31, 2012", 29 pgs.
"International Application Serial No. PCT/US2011/042443, International Search Report dated Nov. 25, 2011", 2 pgs.
"International Application Serial No. PCT/US2011/042443, Response to Written Opinion filed Apr. 27, 2012", 11 pgs.
"International Application Serial No. PCT/US2011/042443, Written Opinion dated Nov. 25, 2011", 4 pgs.
"Canadian Application Serial No. 2,724,339, Office Action dated Jun. 11, 2015", 5 pgs.
"European Application Serial No. 10859869.9, Response filed Dec. 1, 2014 to Extended European Search Report dated May 20, 2014", 26 pgs.
"European Application Serial No. 16190922.1, Extended European Search Report dated Mar. 1, 2017", 7 pgs.
"European Application Serial No. 11804202.7, Communication Pursuant to Article 94(3) and Rule 71(1) EPC dated Mar. 16, 2017", 5 pgs.
"European Application Serial No. 9747584.2, Communication Pursuant to Article 94(3) EPC dated Feb. 20, 2017", 7 pgs.
"Australian Application Serial No. 2009246306, Response filed Sep. 1, 2014 to Office Action dated Mar. 13, 2014", 18 pgs.
"Australian Application Serial No. 2014280969, Non Final Office Action dated Jan. 12, 2015", 2 pgs.
"Australian Application Serial No. 2015202242, First Examiner Report dated May 10, 2016", 3 pgs.
"Australian Application Serial No. 2015202242, Response filed Sep. 21, 2016 to First Examiner Report dated May 10, 2016", 26 pgs.
"Canadian Application Serial No. 2,724,339, Response filed Dec. 11, 2015 to Office Action dated Jun. 11, 2015", (English Translation of Claims), 319 pgs.
"Canadian Application Serial No. 2,880,981, Office Action dated Mar. 8, 2016", 4 pgs.
"Canadian Application Serial No. 2,880,981, Response filed Sep. 7, 2016 to Office Action dated Mar. 8, 2016", 13 pgs.
"European Application Serial No. 09747584.2, Communication Pursuant to Article 94(3) EPC dated Jul. 5, 2016", 7 pgs.
"European Application Serial No. 09747584.2, Response filed Nov. 15, 2016 to Communication Pursuant to Article 94(3) EPC dated Jul. 5, 2016", 16 pgs.
"European Application Serial No. 10859869.9, Examination Notification Art. 94(3) dated Jun. 23, 2015", 4 pgs.
"European Application Serial No. 10859869.9, Response filed Dec. 14, 2015 to Examination Notification Art. 94(3) dated Jun. 23, 2015", 17 pgs.
"European Application Serial No. 11804202.7, Response filed Feb. 3, 2015 to Extended European Search Report dated Jul. 7, 2014", 14 pgs.

(56) References Cited

OTHER PUBLICATIONS

"U.S. Appl. No. 14/597,677, Non Final Office Action dated Nov. 27, 2017", 7 pgs.
"U.S. Appl. No. 14/597,677, Response filed Nov. 8, 2017 to Restriction Requirement dated Jul. 5, 2017", 8 pgs.
"European Application Serial No. 16190922.1, Response filed Sep. 29, 2017 to Extended European Search Report dated Mar. 1, 2017", 18 pgs.

* cited by examiner

REAGENT PREPARATION AND DISPENSING DEVICE

PRIORITY APPLICATIONS

This patent application is a continuation of U.S. patent application Ser. No. 13/988,279, filed Nov. 5, 2013, which claims priority benefit according to 35 U.S.C. 111(a) to International Patent Application serial number PCT/US2010/057238, filed Nov. 18, 2010, and published on May 24, 2012 as WO 2012/067619, which applications and publications are incorporated herein by reference in their entirety.

TECHNICAL FIELD

Storage, preparation and dispensing of solutions.

BACKGROUND

Some examples of diagnostic, life science research and drug discovery reagents require preparation prior to use. For instance, reagents may require measuring a diluent (or solution) and using the diluent to rehydrate a dry reagent. In other examples, preparation of the reagent requires measuring and mixing of a sample solution (e.g., a patient biological sample; an environmental sample such as, water or soil; an agricultural sample such as food and the like) with a reagent in a dried or liquid form. In still other examples, preparation of the reagent requires mixing of two or more liquid components, such as a reagent and another solution.

Manufacturers of diagnostic, life science research and drug discovery reagents use precision and standardized procedures in order to produce high quality reagents. These reagents are often prepared at their point of use. The quality of the reagents (e.g., the precise amount of reagent solution, the purity of the reagent solution and the like) is easily compromised at the point of use because of errors in preparation procedures that are used by personnel responsible for preparing the reagent. For instance, the reagent is handled in an unclean environment having contaminants (e.g., a humid atmosphere; a biologically active environment contaminated with microorganisms, DNA, RNA, ATP and the like; a chemically active environment, and the like), the wrong amount of solution is used, the wrong solution is used, and the like. In other examples, the reagent and solution or diluent are not allowed to mix thoroughly. In still other examples, the reagent solution is dispensed from a device but fails to deliver substantially all of the full specified amount of reagent solution as a result of operator error or device performance (e.g., a significant portion of the solution is left within the device).

Where lyophilized reagents (e.g., dried or freeze-dried reagents) are used, unwanted exposure to contaminants including, but not limited to, moisture or moisture vapor during storage and prior to reconstitution may contaminate or compromise the stability of the lyophilized reagent. Compromising the reagent decreases its ability to rapidly rehydrate thereby creating difficulties in preparing a reagent at the proper concentration. Additionally, compromising the reagent from a dry state (where biological and chemical activities of the reagent are arrested) may reactivate the reagent and allow it to prematurely break down thereby decreasing the effectiveness of the reagent.

Even small errors in preparation leading to an improperly prepared reagent (e.g., mis-measuring of a solution, failure to fully reconstitute the reagent or diluting the reagent and the like) may have undesirable consequences, including, but not limited to, false positives, inaccurate diagnoses leading to inaccurate or inappropriate treatments, and false negatives (undetected diagnoses resulting in no treatment where treatment is needed).

SUMMARY

In Example 1 an apparatus may comprise a body including a reaction chamber including a reagent, and a solution reservoir including a solution, the solution reservoir is isolated from the reaction chamber; a plunger movably coupled with the body, movement of the plunger from a starting position to a seated position pushes the solution into the reaction chamber; a dispensing path extending from the reaction chamber and out of the body, the dispensing path is configured to dispense a reagent mixture formed from the solution and the reagent; and a vent path extending from the reaction chamber, the vent path vents reaction chamber gas displaced by the addition of the solution to the reaction chamber throughout movement of the plunger from the starting position to the seated position.

In Example 2, the apparatus of Example may include a barrel movably coupled with the body, and the plunger is movably coupled with the barrel.

In Example 3, the apparatus of any one or any combination of Examples 1-2 may include the vent path extending through the barrel and along the plunger.

In Example 4, the apparatus of any one or any combination of Examples 1-3 may include the vent path extending along a barrel exterior through a first vent portion, and the vent path extends along a barrel interior through a second vent portion.

In Example 5, the apparatus of any one or any combination of Examples 1-4 may include a semi-permeable media is disposed in the vent path.

In Example 6, the apparatus of any one or any combination of Examples 1-5 may include the dispensing path in a sealed configuration.

In Example 7, the apparatus of any one or any combination of Examples 1-6 may include the dispensing path sealed with a frangible tip.

In Example 8, the apparatus of any one or any combination of Examples 1-7 may include a flushing chamber in the body, the flushing chamber is filled with a flushing fluid operable to push the specified amount of the reagent mixture through the dispensing path.

In Example 9, the apparatus of any one or any combination of Examples 1-8 may include the vent path extending through the flushing chamber.

In Example 10, the apparatus of any one or any combination of Examples 1-9 may include a second plunger operable to close the vent path, and the second plunger is operable to push the flushing fluid through the closed vent path into the reaction chamber.

In Example 11, an apparatus may comprise a body including a reaction chamber including a reagent, and a solution reservoir including a solution, the solution reservoir is isolated from the reaction chamber; a plunger movably coupled with the body, movement of the plunger pushes the solution into the reaction chamber; a dispensing path extending from the reaction chamber and out of the body, the dispensing path is configured to deliver a reagent mixture formed from the solution and the reagent; a flushing chamber including a flushing fluid in communication with the reaction chamber; and a vent path extending from the reaction chamber, the vent path includes open and closed configurations: in the open configuration, the vent path extend outside of the body, and the vent path vents reaction chamber gas displaced by the addition of the solution to the reaction chamber, and in the closed configuration, the vent path is closed, and flushing fluid delivered from the flushing chamber dispenses the reagent mixture through the dispensing path.

In Example 12, the apparatus of Example 11 may include a barrel movably coupled with the body, and the plunger is movably coupled with the barrel.

In Example 13, the apparatus of any one or any combination of Examples 11-12 may include the vent path extending through the barrel and along the plunger.

In Example 14, the apparatus of any one or any combination of Examples 11-13 may include the vent path extending along a barrel exterior through a first vent portion, and the vent path extends along a barrel interior through a second vent portion.

In Example 15, the apparatus of any one or any combination of Examples 11-14 may include a semi-permeable media disposed in the vent path.

In Example 16, the apparatus of any one or any combination of Examples 11-15 may include a sealed dispensing path.

In Example 17, the apparatus of any one or any combination of Examples 11-16 may include the dispensing path sealed with a frangible tip.

In Example 18, the apparatus of any one or any combination of Examples 11-17 may include the vent path extending through the flushing chamber.

In Example 19, the apparatus of any one or any combination of Examples 11-18 may include a second plunger operable to close the vent path, and the second plunger is operable to push the flushing fluid through the closed vent path into the reaction chamber.

In Example 20 an apparatus may comprise a body including a reaction chamber including a reagent, and a solution reservoir including a solution, the solution reservoir is isolated from the reaction chamber; a first plunger movably coupled with the body, movement of the first plunger pushes the solution into the reaction chamber with the reagent to form a reagent mixture; a second plunger movably coupled with the body, movement of the second plunger dispenses a specified amount of the reagent mixture from the body; and a vent path in communication with the reaction chamber, the vent path includes open and closed configurations: in the open configuration, the vent path extends from the reaction chamber to outside of the body, and the vent path vents gas displaced from the reaction chamber by the addition of the solution to the reaction chamber, and in the closed configuration, the vent path is closed.

In Example 21, the apparatus of Examples 20 may include the second plunger movable to close the vent path.

In Example 22, the apparatus of any one or any combination of Examples 20-21 may include the body including a flushing chamber containing a flushing fluid.

In Example 23, the apparatus of any one or any combination of Examples 20-22 may include the flushing chamber in communication with the vent path and the reaction chamber, and the second plunger is operable to push flushing fluid into the reaction chamber through the vent path in the closed configuration.

In Example 24, the apparatus of any one or any combination of Examples 20-23 may include the flushing chamber formed by the second plunger and a vent wall.

In Example 25, the apparatus of any one or any combination of Examples 20-24 may include a volume of the flushing chamber greater than a volume of the reaction chamber.

In Example 26, the apparatus of any one or any combination of Examples 20-25 may include the vent path extending from the reaction chamber between the body and a barrel movably coupled with the body.

In Example 27, the apparatus of any one or any combination of Examples 20-26 may include a semi-permeable media disposed in the vent path, the semi-permeable media retains the reagent mixture but not gas within the reaction chamber.

In Example 28 a method may include positioning a solution within a body; positioning a reagent within a reaction chamber in the body, the reagent is isolated from the solution; movably coupling an activator with the body, the activator is movable to force the solution into the reaction chamber and form a reagent mixture when the activator is moved from a starting position to a seated position; forming a closed dispensing tip extending from the reaction chamber and out of the body; and forming a vent path extending from the reaction chamber to outside of the body, the vent path vents gas from the reaction chamber displaced by the addition of the solution to the reaction chamber, and the vent path vents gas throughout movement of the activator from the starting position to the seated position.

In Example 29, the method of Example 28 may include movably coupling the activator with the body including movably coupling a plunger with the body.

In Example 30, the method of any one or any combination of Examples 28-29 may include forming the closed dispensing tip includes forming a frangible dispensing tip.

In Example 31, the method of any one or any combination of Examples 28-30 may include movably coupling a barrel with the body.

In Example 32, the method of any one or any combination of Examples 28-31 may include forming the vent path including extending the vent path between the barrel and the body.

In Example 33, the method of any one or any combination of Examples 28-32 may include forming the vent path including forming the vent path through the body from the reaction chamber, and forming the closed dispensing tip includes forming the closed dispensing tip extending from the reaction chamber in an opposed direction to the vent path.

In Example 34, the method of any one or any combination of Examples 28-33 may include forming a flushing chamber within the body, and the flushing chamber is in fluid communication with the reaction chamber through the vent path.

In Example 35, the method of any one or any combination of Examples 28-34 may include movably coupling a second plunger with the body, and the second plunger is operable to close the vent path and push a flushing fluid through the vent path into the reaction chamber.

In Example 36, the method of any one or any combination of Examples 28-35 may include forming the closed dispensing tip including extending the closed dispensing tip from a first portion of the reaction chamber, and forming the vent path includes extending the vent path from a second portion of the reaction chamber opposed to the first portion.

In Example 37 a method may include opening a sealed reaction chamber within a body, the reaction chamber containing a reagent; reconstituting the reagent with a solution retained within the body to form a reagent mixture, reconstituting including adding the solution to the reaction chamber; venting displaced gas from the reaction chamber, the gas is displaced by addition of the solution, the vented gas passing through a vent path extending through the body away from a dispensing tip; and dispensing a specified amount of the reagent mixture, dispensing including closing the vent path and pushing a flushing fluid through the vent path into the reaction chamber.

In Example 38, the method of Example 37 may include venting gas including preventing pressurization within the reaction chamber during reconstitution.

In Example 39, the method of any one or any combination of Examples 37-38 may include dispensing the specified amount of the reagent mixture including pressurizing the reaction chamber.

In Example 40, the method of any one or any combination of Examples 37-39 may include venting gas including venting gas through the body in a direction opposed to a direction of dispensing the specified amount of the reagent mixture.

In Example 41, the method of any one or any combination of Examples 37-40 may include reconstituting the reagent adjacent to the dispensing tip in a first portion of the reaction chamber, and the gas is vented from a second portion of the reaction chamber remote from the first portion.

In Example 42, the method of any one or any combination of Examples 37-41 may include reconstituting and dispensing of the specified amount of the reagent mixture are performed with the body in substantially the same orientation.

In Example 43, the method of any one or any combination of Examples 37-42 may include dispensing the specified amount of the reagent mixture including moving a plunger relative to the body, and closing the vent path includes engaging the plunger with a vent wall to seal a flushing chamber formed by the plunger and the vent wall, and pushing the flushing fluid through the vent path includes moving the plunger through the flushing chamber.

In Example 44, the method of any one or any combination of Examples 37-43 may include removing a frangible portion of the dispensing tip.

In Example 45 an apparatus may include a body including a reaction chamber including a reagent, and a solution reservoir including a solution, the solution reservoir is isolated from the reaction chamber; a plunger movably coupled with the body, movement of the plunger from a starting position to a seated position pushes the solution into the reaction chamber; a dispensing path extending from the reaction chamber and out of the body, the dispensing path is configured to dispense a reagent mixture formed from the solution and the reagent; and venting means configured to vent gas displaced by the addition of the solution to the reaction chamber.

In Example 46 the apparatus of Example 45 may include the venting means including a vent path extending from the reaction chamber.

In Example 47, the apparatus of any one or any combination of Examples 45-46 may include barrel movably coupled with the body, and the plunger is movably coupled with the barrel.

In Example 48, the apparatus of any one or any combination of Examples 45-47 may include the venting means extending at least partially through the barrel and along the plunger.

In Example 49, the apparatus of any one or any combination of Examples 45-48 may include the venting means extending along a barrel exterior through a first vent portion, and the venting means extends along a barrel interior through a second vent portion.

In Example 50, the apparatus of any one or any combination of Examples 45-49 may include the venting means including a semi-permeable media.

In Example 51, the apparatus of any one or any combination of Examples 45-50 may include a sealed dispensing path.

In Example 52, the apparatus of any one or any combination of Examples 45-51 may include the dispensing path sealed with a frangible tip.

In Example 53, the apparatus of any one or any combination of Examples 45-46 may include flushing means configured to force flushing fluid into the reaction chamber to push a specified amount of the reagent mixture through the dispensing path.

In Example 54, the apparatus of any one or any combination of Examples 45-53 may include the venting means extending through the flushing chamber.

In Example 55, the apparatus of any one or any combination of Examples 45-54 may include a second plunger operable to close the venting means, and the second plunger is operable to push the flushing fluid through the closed venting means into the reaction chamber.

In Example 56, the apparatus or method of any one or any combination of Examples herein is configured to form a specified volume of reagent mixture from about 10 to 100 micro liters with 10 percent or better precision.

In Example 57, the apparatus or method of any one or any combination of Examples herein is configured to dispense around at least 80 percent of the specified volume of the reagent mixture formed in the reaction chamber.

In Example 58, the apparatus or method of any one or any combination of Examples herein is configured to form a specified volume of reagent mixture from about 10 to 200 micro liters with 10 percent or better precision.

In Example 59, the apparatus or method of any one or any combination of Examples herein is configured to dispense at least around 90 percent of the specified volume of the reagent mixture formed in the reaction chamber.

DESCRIPTION OF THE EMBODIMENTS

In the following detailed description, reference is made to the accompanying drawings which form a part hereof, and in which is shown by way of illustration specific embodiments in which the disclosure may be practiced. These embodiments are described in sufficient detail to enable those skilled in the art to practice the disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents. While the devices and methods presented in the detailed description describe devices for uses, non-pharmaceutical uses and the like, the devices and methods are applicable to at least some pharmaceutical applications that do not require administration to a subject by injection with a syringe needle. Additionally, the reagents described below include, but are not limited to, lyophilized reagents, liquid reagents, powder reagents and the like. Further, the solutions described below include, but are not limited to, liquid solutions such as, saline, distilled water, tap water, pH buffered water, chemical solutions capable of breaking down the reagents and the like. In another example, the solutions include, but are not limited to, biological or environmental samples in a liquid form or suspended within a liquid, such as blood, urine, fecal matter, saliva, perspiration, soil, ground water, fresh water, salt water, explosives, explosive residues, toxins and the like.

Figure 1:
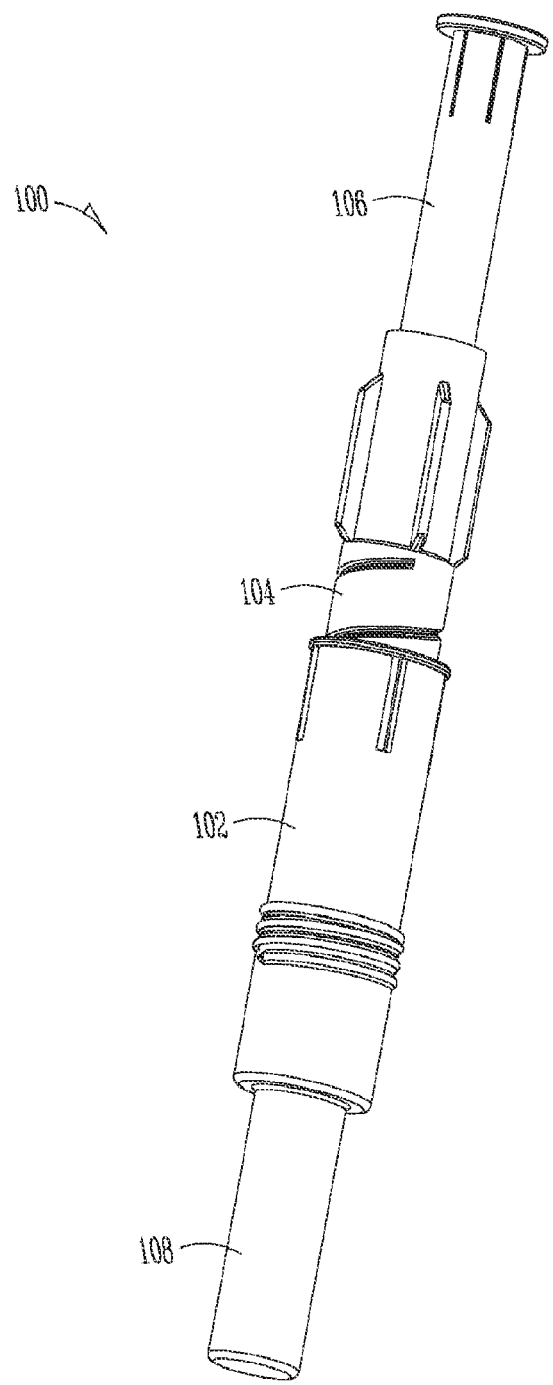
FIG. 1 is a perspective view of one example of a reagent preparation and dispensing device.

FIG. 1 shows one example of a reagent preparation and dispensing device 100. As shown, the device 100 includes a body 102 movably coupled with a barrel 104. The device 100 further includes an activator 106 movably coupled relative to the barrel 104 and the body 102. A cap 108 is positioned over a dispensing tip coupled with the body 102. The components of the reagent preparation and dispensing device 100 described herein are constructed with but not limited to metals, plastics and other materials capable of maintaining a dry and sterile environment within the device 100. For instance, the reagent preparation and dispensing device 100 is constructed with stainless steel in one embodiment. In another example, the device 100 is constructed with a plastic including, but not limited to, Polypropylene, Polyethylene, Polycarbonate, Acrylic, ABS, Polystyrene, combinations of these plastics, combinations with metals and the like. While in the configuration shown in FIG. 1, the body 102, barrel 104 and cap 108 cooperate to store a reagent within the reagent preparation and dispensing device 100 and substantially prevent the interaction of the reagent with moisture such as ambient humidity. In some examples, the reagent within the reagent preparation and dispensing device 100 is kept in a freeze-dried or lyophilized form and reconstitution of the reagent is performed through the addition of fluids, such as water, to the reagent.

Figure 2A:
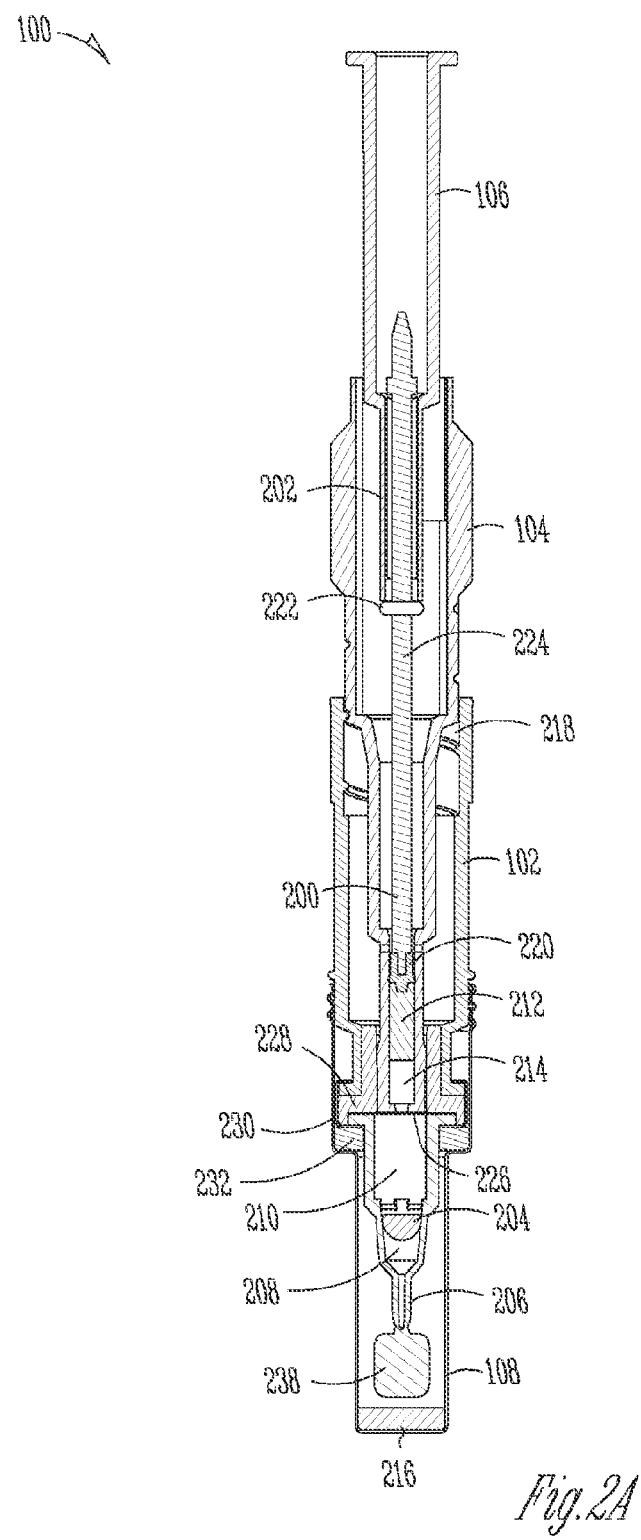
FIG. 2A is a cross-sectional view of the device shown in FIG. 1.
Figure 2B:
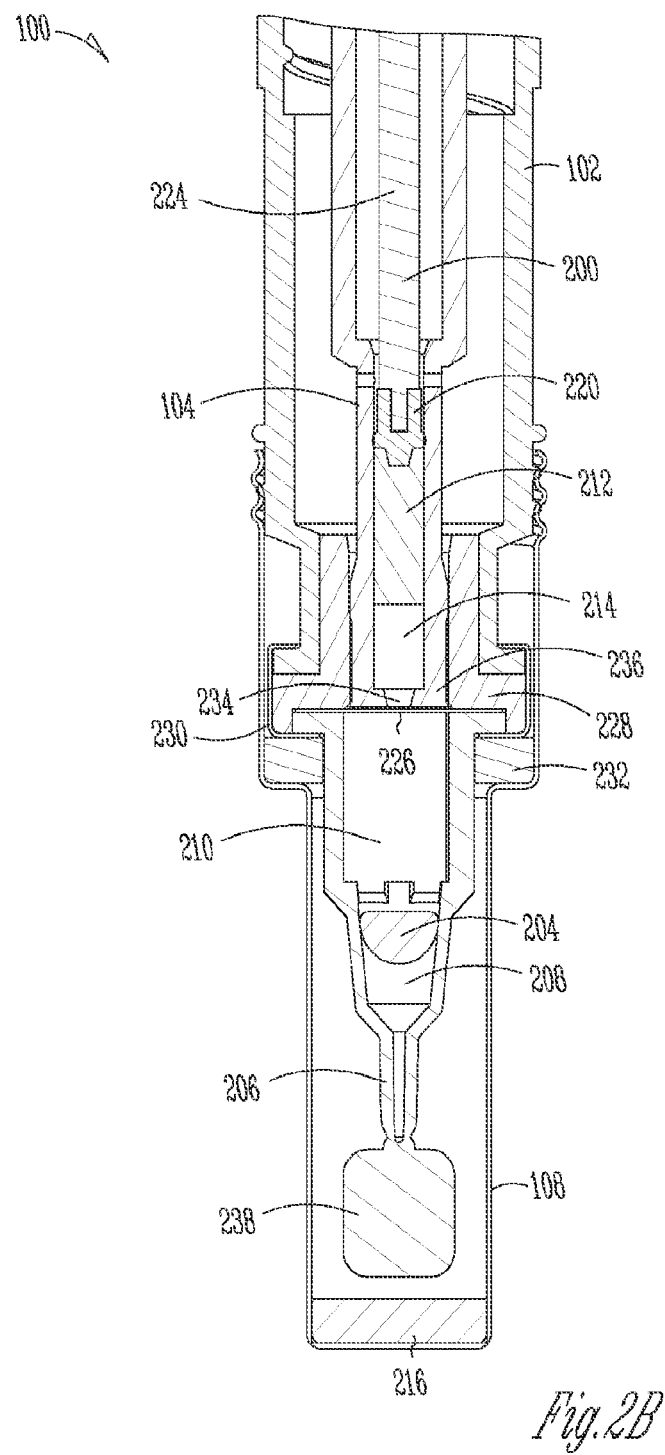
FIG. 2B is a detailed cross sectional view of a portion of the device shown in FIG. 3A.

Referring now to FIG. 2A, the reagent preparation and dispensing device 100 is shown in an as-shipped configuration previously presented in FIG. 1. The reagent preparation and dispensing device 100 includes a solution reservoir 214 containing a solution 212 (e.g., a diluent). As shown in the example of FIG. 2A, the solution reservoir 214 is retained within a portion of the barrel 104. A first plunger 200 extends through the barrel 104. In one example, the plunger 200 includes a first plunger gasket 220 positioned immediately above the solution reservoir 214. The first plunger 200 closes the solution reservoir 214 at one end. A reservoir seal 226 is positioned across a solution nozzle 234 formed at the end of the barrel 104, as shown in FIG. 2B. The reservoir seal 226 closes the opposed end of the solution reservoir 214 thereby isolating the solution 212 from a reagent 204 shown in the reagent reservoir 210.

The reagent reservoir 210 sized and shaped to retain the reagent 204. As previously described, in one example, the reagent 204 includes but is not limited to a freeze-dried or lyophilized reagent capable of rapid reconstitution when introduced to a liquid, such as solution 212. As described in further detail below, the reagent reservoir 210 includes a reaction chamber 208 as shown in FIGS. 2A and 2B. The reaction chamber 208 is sized and shaped to receive the reagent 204 therein. During reconstitution the barrel 104 is advanced into the reagent reservoir 210 and the solution and the reagent 204 are reconstituted within the reaction chamber 208 as opposed to the entire reagent reservoir 210. The reaction chamber 208 is in communication with a dispensing tip 206. The dispensing tip 206 as shown in FIGS. 2A and 2B is sealed by a frangible tip 238. The frangible tip 238 is sized and shaped to detach from the dispensing tip 206 when dispensing of the reconstituted reagent is desired.

Referring now to FIG. 2A, the reagent preparation and dispensing device 100 includes first and second plungers 200, 202. As previously described, the first plunger 200 is movably coupled with the barrel 104. The second plunger 202 is moveably coupled around the first plunger shaft 224. In the example shown, each of the first and second plungers 200, 202 includes corresponding gaskets, such as the first plunger gasket 220 and the second plunger gasket 222. As will be described in further detail below, the first plunger gasket 220 tightly engages with the interior surface of the barrel 104 to force the solution 212 through the solution nozzle 234 and into the reaction chamber 208 when reconstitution of the reagent 204 is desired. Sliding engagement of the second plunger gasket 222 with the interior of the barrel 104 seals a portion of the barrel and forces a flushing gas through the barrel interior into the reaction chamber 208 for dispensing of the reconstituted reagent. The activator 106 is provided to actuate both the first plunger 200 and the second plunger 202. As described in further detail below, one or more of the barrel 104, first plunger 200 (including the first plunger shaft 224) and the second plunger 202 include a series of mechanical interfittings sized and shaped to selectively permit movement of one or more of the first and second plungers 200, 202 relative to each other and relative to the barrel 104. Engagement of the mechanical interfittings, in some configurations, prevents movement of one or more of the first plunger 200 and second plunger 202 relative to each other or relative to the barrel 104.

Referring now to FIG. 2B, a detailed view of the reagent preparation and dispensing device 100 is shown including a piercing surface 236 of the barrel 104. As previously described, a reservoir seal 226 is interposed between the solution reservoir 214 and the reagent reservoir 210. Movement of the barrel 104 relative to the body 102 moves the barrel piercing surface 236 through the reservoir seal 226 to pierce the seal and allowing communication between the solution reservoir 214 and the reagent reservoir 210. Referring to FIG. 2A, in one example, the mechanical fitting 218 is formed between the body 102 and barrel 104. The mechanical fitting 218 includes, but is not limited to, features that facilitate movement of the barrel 104 relative to the body 102 such as, threading, slidable couplings and the like. In the example shown in FIGS. 2A and 2B, rotation of the barrel 104 relative to the body 102 translates the barrel 104 into engagement with the reservoir seal 226 through engagement between corresponding threading of the barrel 104 and the body 102. As will be described in further detail below, after penetration of the reservoir seal 226 by the barrel 104 the first plunger 200 is actuated to force the solution 212 out of the solution reservoir 214 and into the reaction chamber 208 containing the reagent 204.

As previously described, the reagent preparation and dispensing device 100 is configured to ensure the reagent 204 such as a freeze dried reagent is substantially isolated from moisture and fluid until reconstitution is desired. Referring to FIG. 2B, the body 102 and dispensing tip 206 are coupled together with an interconnecting gasket 228 interposed therebetween. A crimp sleeve 230 is crimped around the interconnecting gasket 228 and adjacent portions of the body 102 and the dispensing tip 206. In one example, the crimp sleeve 230 and the interconnecting gasket 228 are constructed with materials that substantially prevent the ingress of moisture into the reagent reservoir 210. For instance, the interconnecting gasket 228 is formed with a non-reticulated foam, solid rubber, an elastomer, and the like. The crimp sleeve 230 is formed with a metal such as stainless steel, aluminum and the like. Crimping of the crimp sleeve 230 around the interconnecting gasket 228 substantially prevents the ingress of moisture between the reservoir seal 226 and the dispensing tip 206. Additionally, a desiccant 216 is provided at the bottom of the cap 108 to substantially absorb any moisture present within the cap 108 at the assembly of the reagent preparation and dispensing device 100, during transport and immediately prior to use. In yet another example, the cap 108 is constructed with metal, such as stainless steel or aluminum, configured to substantially prevent the ingress of moisture through the cap. Further, as shown in FIGS. 2A and 2B the dispensing tip 206 includes a frangible tip 238 coupled thereto. The frangible tip provides a sealed feature on the dispensing tip 206 to substantially prevent the ingress of moisture and fluids into the reagent reservoir 210 through the dispensing path used after reconstitution to dispense the reconstituted reagent from the device 100 (e.g., the lumen from the reaction chamber 208 to exterior of the device 100).

Figure 3A:
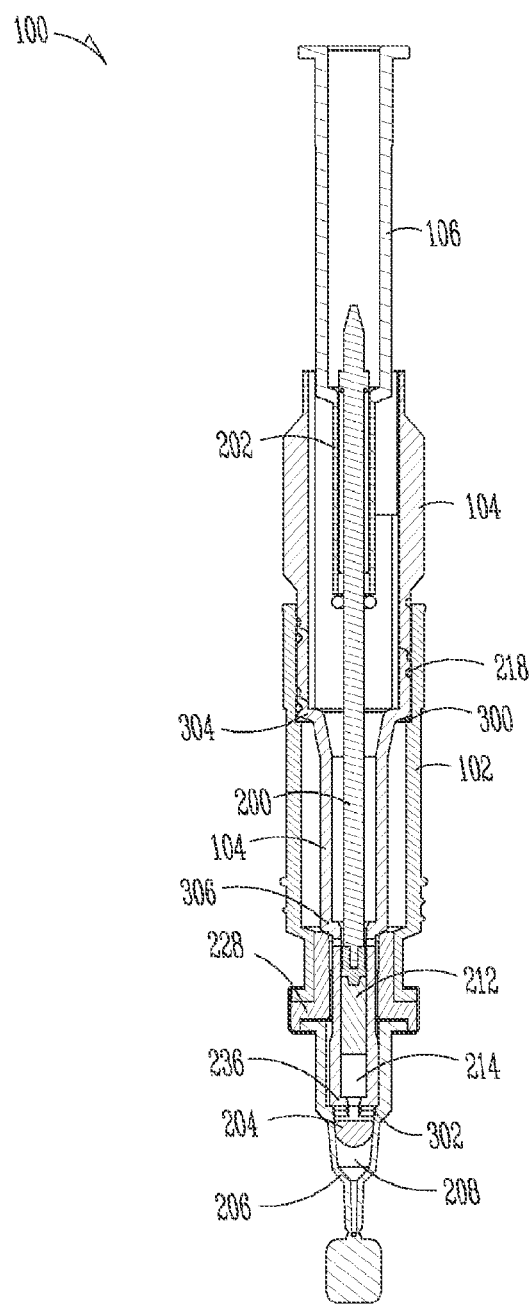
FIG. 3A is a cross sectional view of the device shown in FIG. 1.
Figure 3B:
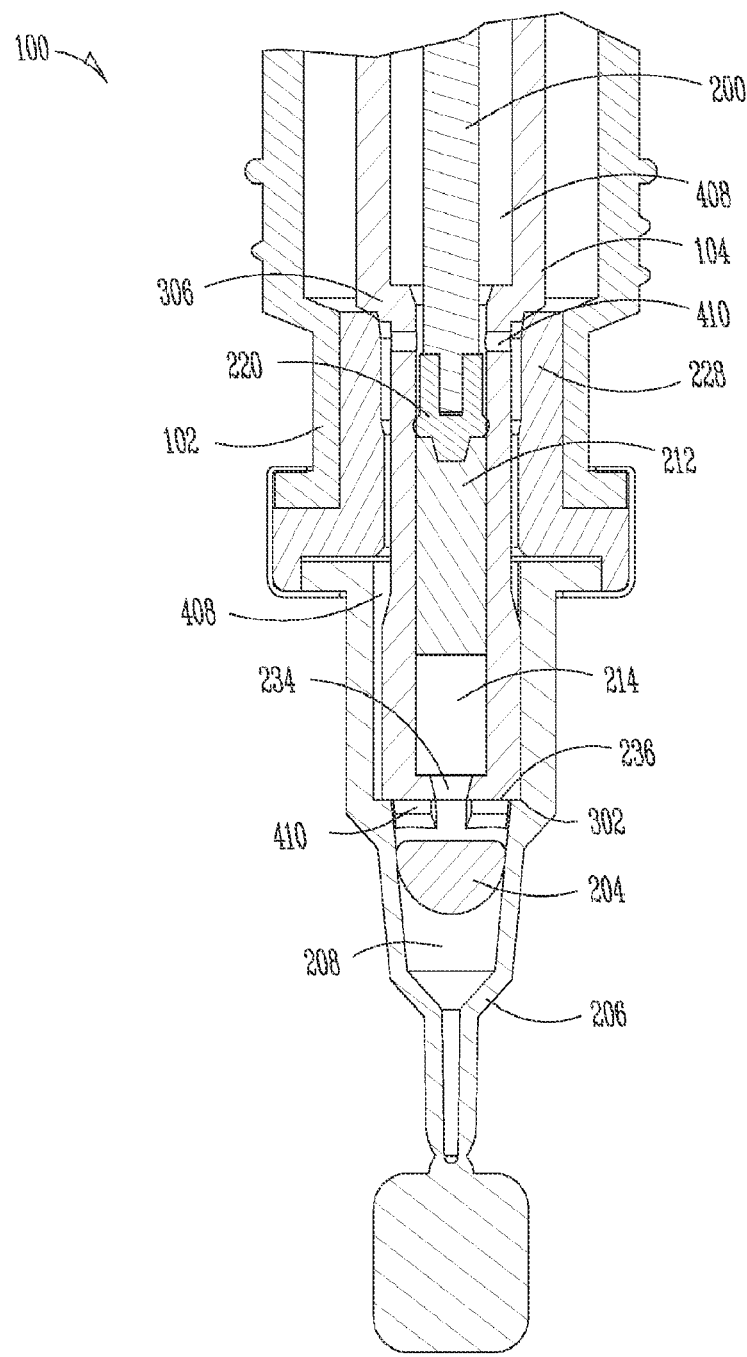
FIG. 3B is a detailed cross sectional view of a portion of the device shown in FIG. 3A.

FIGS. 3A and 3B show the reagent preparation and dispensing device 100 in a first intermediate configuration. As previously described, the barrel 104 is movable relative to the body 102. Referring first to FIG. 3A, the barrel 104 is translated relative to body 102 with the barrel piercing surface 236 penetrating through the reservoir seal 226 (see FIGS. 2A and 2B). Penetration of the reservoir seal 226 allows for communication between the solution reservoir 214 and the reaction chamber 208 containing the reagent 204. Movement of the activator and the first plunger 200 relative to the barrel 104 as described below pushes the solution 212 in the solution reservoir 214 through the solution nozzle 234 into the reaction chamber 208. The addition of the solution 212 to the reaction chamber 208 reconstitutes the reagent 204 into a reagent mixture for eventual dispensing through the dispensing tip 206.

Movement of the barrel 104 including the piercing surface 236 into the reagent reservoir 210 (see FIGS. 2A and 2B) fills a portion of the reagent reservoir 210 thereby leaving the reagent 204 within the reaction chamber 208 for interaction with the solution 212 from the solution reservoir 214. The barrel is sized and shaped for reception within the reagent reservoir 210 and seating therein to define the reaction chamber 208 as shown in FIGS. 3A and 3B. For instance, the barrel includes the piercing surface 236 and the dispensing tip 206 includes a second barrel stop 302 sized and shaped to engage with the piercing surface 236 and receive the piercing surface after full translation of the barrel 104 into the selected region of the reagent reservoir 210 as shown in FIGS. 3A and 3B. Engagement of the second barrel stop 302 with the piercing surface 236 arrests further movement of the barrel 104 thereby maintaining a specified volume within the reaction chamber 208 for reconstitution of the reagent 204.

In another example, the reagent preparation and dispensing device 100 includes a first barrel stop 300 included with the body 102. A First barrel flange 304 on the body 104 is sized and shaped to engage with the first barrel stop 302 and arrest further movement of the barrel 104 into the body 102. In a similar manner to the second barrel stop 302 and the piercing surface 236, the first barrel stop 300 and first barrel flange 304 arrest movement of the piercing surface 236 thereby maintaining a consistent volume in the reaction chamber 208 for reconstitution of the reagent 204. As previously described in at least one example, a mechanical fitting 218 is formed between the body 102 and the barrel 104. In one example, rotation of the barrel 104 relative to the body 102 longitudinally moves the barrel 104 into the body 102, for instance, penetrating the piercing surface 236 through the reservoir seal 226 to facilitate reconstitution of the reagent 204. As the barrel 104 is rotated relative to the body 102 the first barrel flange 304 at one end of the threading of the mechanical fitting 218 engages against the first barrel stop 300 to arrest further movement of the barrel 104 through rotation into the body 102. Seating of the barrel within the reagent reservoir 210 shrinks the reservoir to include only the reaction chamber 208 and ensures the solution 212 interacts with the reagent 204 in the smaller space. Unintended separation of the solution 212 from the reagent 204 is thereby avoided.

The barrel further includes a vent flange 306 sized and shaped to engage with the interconnecting gasket 228. Engagement of the vent flange 306 with the interconnecting gasket 228 tightly seals the portion of the barrel extending from the vent flange 306 to the piercing surface 236. As will be described in further detail below, engagement of the vent flange 306 with the interconnecting gasket 328 forms a sealed passage for venting of gases from the reaction chamber 208 during reconstitution of the reagent 204. Referring to FIG. 3A, in one example, the first barrel stop, second barrel stop 300, 302 and the first barrel flange 304 and piercing surface 236 of the barrel 104, dispensing tip 206 and body 102 are sized and shaped to position the barrel 104 after movement into the body 102 so the vent flange 306 tightly engages with the interconnecting gasket 228 to form the seal therebetween. Stated another way, as the first barrel flange 304 engages with the first barrel stop 300 and the piercing surface 236 correspondingly engages with the second barrel stop 302 the vent flange 306 is engaged with and seals against the interconnecting gasket 228 to form a sealed vent path.

Figure 3C:
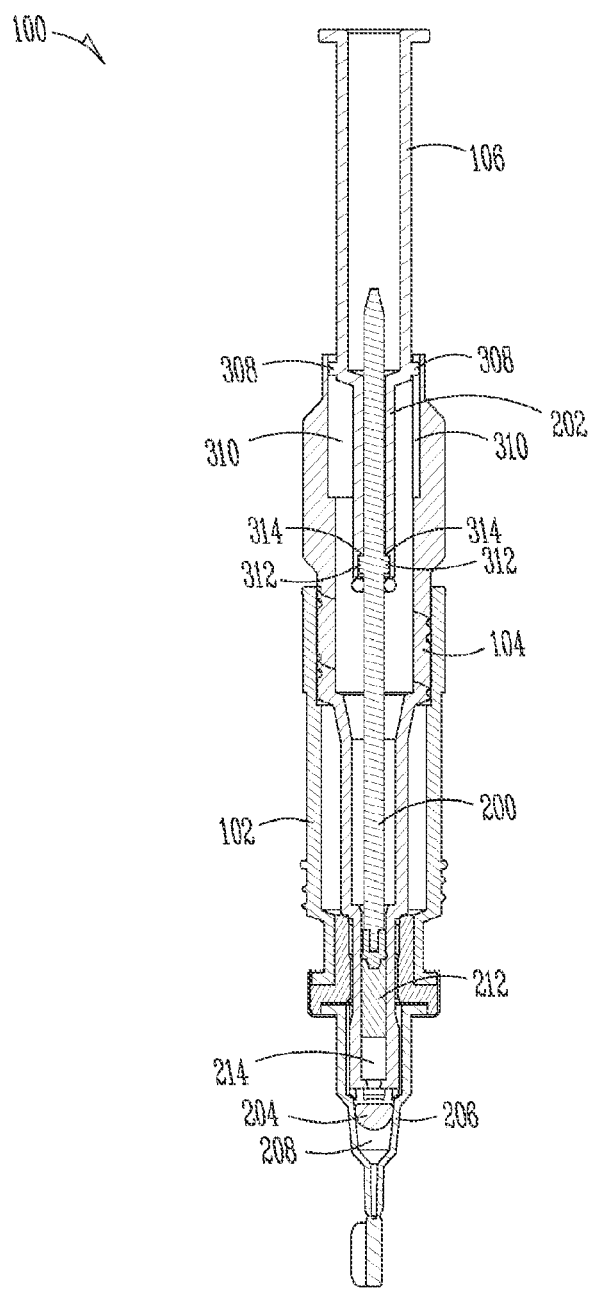
FIG. 3C is a cross sectional view of the device shown in FIG. 3A rotated to show activator lugs positioned within first barrel slots, and first plunger lugs engaged with activator stops.

FIG. 3C shows another view of the reagent preparation and dispensing device 100 previously shown in FIGS. 3A and 3B. The view shown in FIG. 3C is rotated relative to those of FIGS. 3A, B to illustrate differing features, as describe below. As previously described the barrel 104 is advanced into the body 102 to pierce a reservoir seal 226 shown in FIG. 2A. As will be described in further detail below, depression of the activator 106 while the reagent preparation and dispensing device 100 is in the configuration shown in FIG. 3C correspondingly moves the first plunger 200 through the solution reservoir 214 thereby pushing the solution 212 into the reaction chamber 208 containing the reagent 204. As shown in FIG. 3C, a series of lugs, slots and stops are selectively engaged to fix the activator 106 relative to the first plunger 200 so that depression of the activator 106 correspondingly moves the first plunger 200. For instance, the first plunger 200 includes plunger lugs 312 sized and shaped for engagement with activator stops 314 formed in the activator 106 (e.g., near an end of the second plunger 202). Selective engagement of the activator stops 314 and the plunger lugs 312 transmits longitudinal movement from the activator 106 to the first plunger 200 to thereby push the solution 212 out of the solution reservoir 214 for reconstitution of the reagent 204.

In yet another example, the activator 106 includes activator lugs 308 sized and shaped for reception within first barrel slots 310 of the barrel 104. While the activator lugs 308 are received within the first barrel slots 310 the activator 106 and the first plunger 200 selectively engaged with the activator are longitudinally movable relative to the barrel 104. Stated another way, the activator lugs 308 are slidably received within the first barrel slots 310 to facilitate longitudinal movement of the activator 106 and first plunger 200 relative to the barrel 104. As will be described in further detail below, the activator lugs 308 and plunger lugs 312 are respectively positionable within the corresponding barrel slots 310 and engaged with the activator stops 314 to lock and unlock the activator 106 relative to the barrel 104 and also selectively engage and disengage the first plunger 200 from the activator 106. By selectively engaging and disengaging the barrel 104, the activator 106 and the first plunger 200, relative movement between these components is permitted or prevented at various steps during reconstitution and dispensing of the reagent solution through the dispensing tip 206.

Figure 4A:
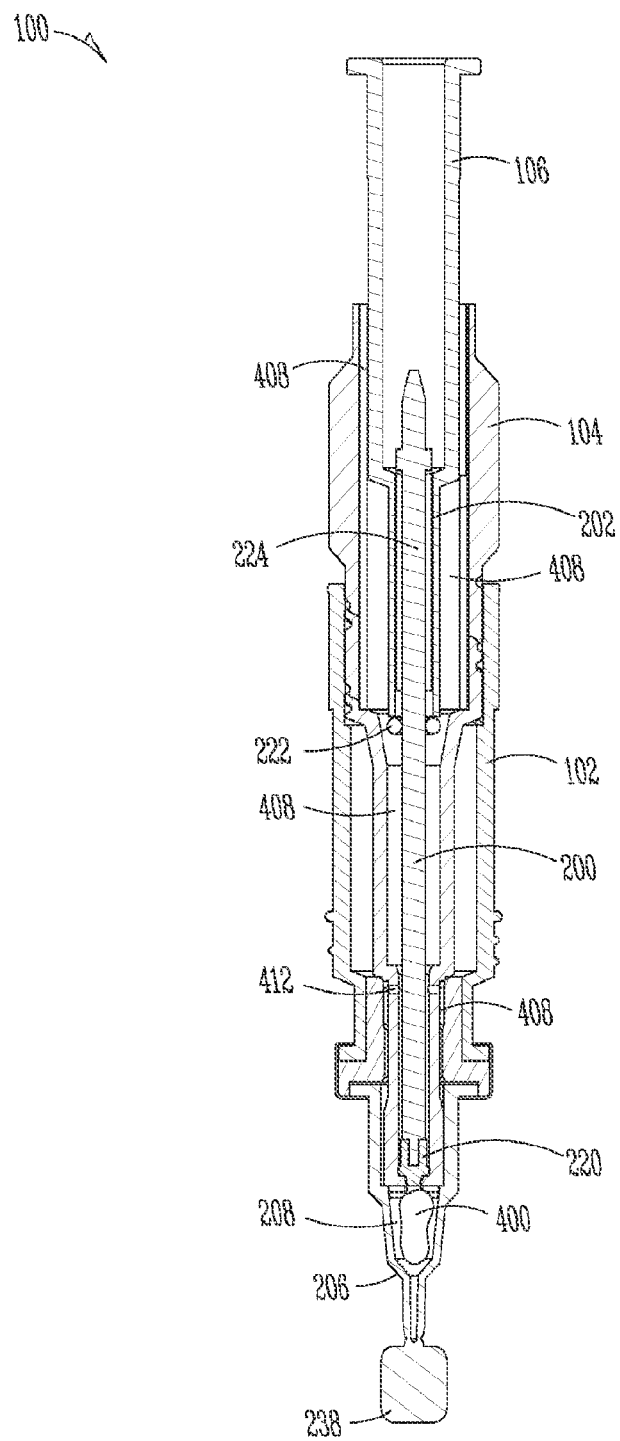
FIG. 4A is a cross sectional view of the device shown in FIG. 3A with the solution introduced to the reagent.
Figure 4B:
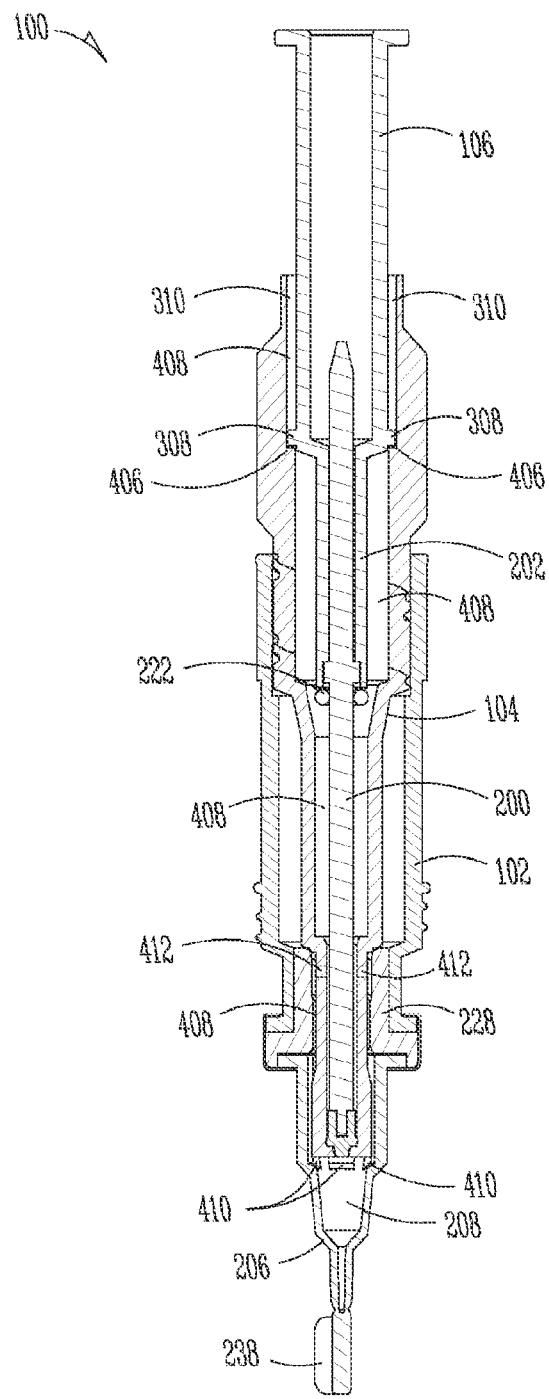
FIG. 4B is a cross sectional view of the device shown in FIG. 4A rotated 90 degrees about the device longitudinal axis.
Figure 4C:
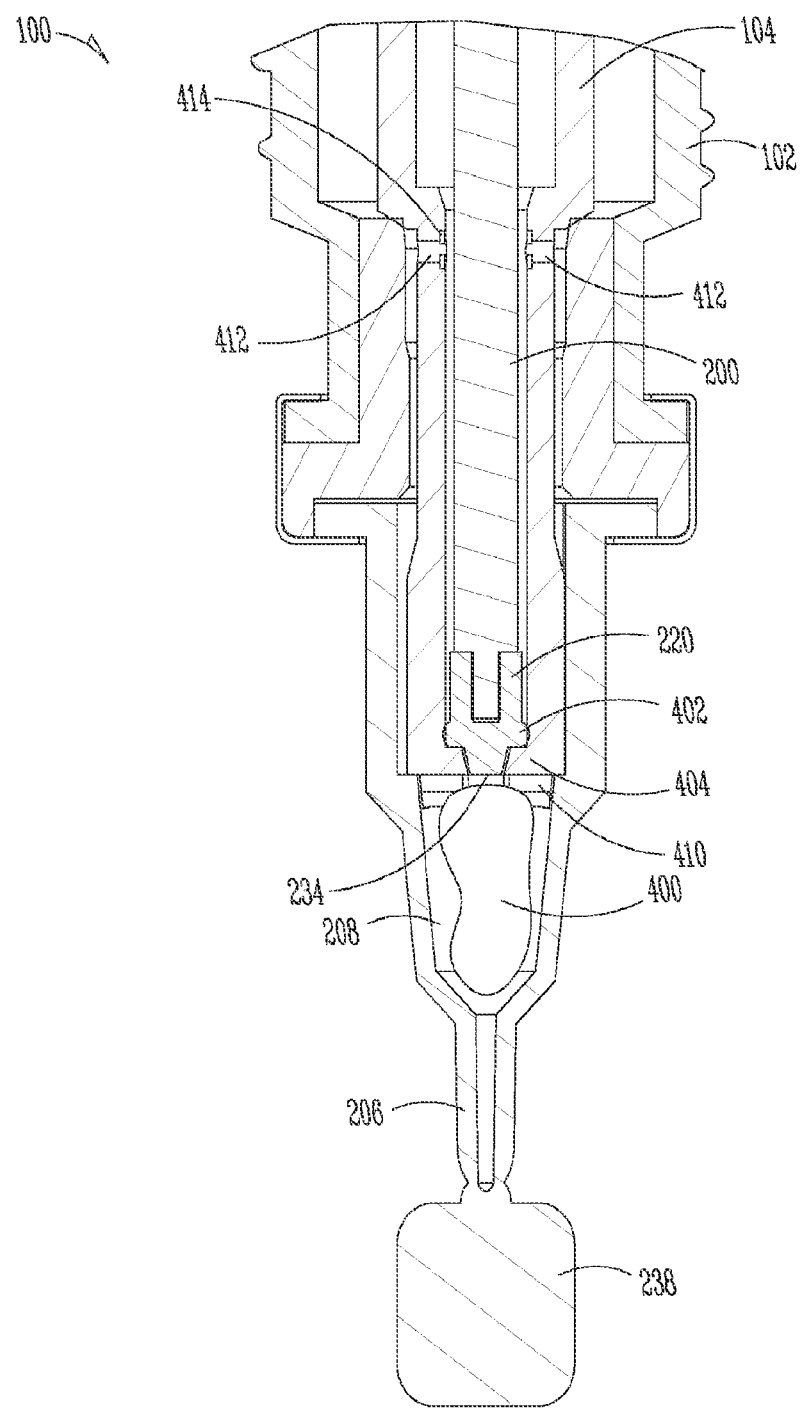
FIG. 4C is a detailed cross sectional view of a portion of the device shown in FIG. 4A.

FIGS. 4A-C show the reagent preparation and dispensing device 100 in a second intermediate configuration. As shown in FIG. 4A, the activator 106 is moved relative to the barrel 104 and body 102 to position the plunger 200 in the orientation shown in FIG. 4A. As will be described in further detail below, the activator 106 is engaged with the plunger 200 and longitudinal movement of the activator 106 is transmitted to the plunger 200. As shown in FIG. 4A, the activator 106, in one example, is integral to the second plunger 202. When moved the activator 106, the second plunger 202 and the first plunger 200 move as a single assembly while the activator 106 is longitudinally fixed relative to the first plunger 200. Referring back to FIG. 2A, the activator 106 and the first plunger 200 are shown in a starting position where the first plunger 200 and the first plunger gasket 220 are positioned at one end of the solution reservoir 214 and the solution 212 is retained within the reservoir. After translation of the barrel 104 relative to the body 102, the activator 106, second plunger 202 and first plunger 200 along with the solution reservoir 214 are translated into the dispensing tip 206 (e.g., the reagent reservoir 210). While in the orientation shown in FIG. 3A, the activator 106 and first plunger 200 are held statically relative to the body 104 and the solution 212 is not forced out of the solution reservoir 214. Stated another way the plunger 200 remains in the starting position shown in FIG. 2A while the barrel 104 is advanced into the reagent reservoir 210 and the reservoir seal 226 shown in FIG. 2B is penetrated.

Referring again to FIG. 4A, the first plunger 200 is moved relative to the body 104 by the activator 106, for instance, the technician depresses the activator 106 to move the first plunger 200 into the seated position shown in FIG. 4A. As the first plunger 200 is advanced through the solution reservoir 214 the solution 212 is pushed into the reaction chamber 208. Movement of the first plunger 200 from the starting position shown in FIGS. 2A, 3A to the seated position shown in FIG. 4A forces the entirety of the solution 212 through the solution nozzle 234 shown in FIGS. 2A and 2B (and 4C). The solution reservoir 214 is thereby substantially eliminated to prevent retention of the solution 212 therein. Introduction of the solution into the reaction chamber 208 reconstitutes the reagent 204 forming a reagent mixture 400 (e.g., a reagent solution or reconstituted reagent).

Referring now to FIG. 4C, the first plunger 200 is advanced to push the entirety of the solution into the reaction chamber 208 as described above. As shown, the plunger includes a plunger flange 402 sized and shaped to engage with the plunger seat 404 when the plunger 200 reaches the seated position shown in FIG. 4C. Engagement of the plunger flange 402 (e.g., a part of the first plunger gasket 220) with the plunger seat 404 provides affirmative notification to the technician using the reagent preparation and dispensing device 100 that the entirety of the solution has been transmitted to the reaction chamber 208 for reconstitution of the reagent 204. Residual solution within the solution reservoir 214 (and not used in reconstitution) is thereby avoided. In another example, where the plunger 200 includes the first plunger gasket 220, the first plunger gasket wipes any remaining solution from the interior of the solution reservoir 214 and forces it through the solution nozzle 234 interposed between the solution reservoir 214 and reaction chamber 208. After actuation of the activator 106 and the first plunger 200 into the seated position shown in FIGS. 4A-C, because of the affirmative seating of the first plunger 200 as shown it is clear to the technician that the entirety of the solution has been added to the reaction chamber 208.

With the features described herein, for instance the shrinking of the reaction chamber 208, seating of the plunger 200 at the plunger seat 404 to substantially eliminate the solution reservoir 214 and the like, consistent and reliable reconstitution of relatively small volumes of reagent is achieved (i.e., at the micro liter scale). In one example, the reagent preparation and dispensing device 100 is configured to reconstitute a specified volume of reagent between around 10 to 300 micro liters (e.g., the device 100 is configured to reconstitute one of 10, 20, 100, 200 or 300 and the like micro liters of reagent). In another example, the reagent preparation and dispensing device is configured to reconstitute between around 10 to 200 micro liters. In still another example, the reagent preparation and dispensing device 100 is configured to reconstitute between around 10 to 100 micro liters. Because of the precise construction of the device 100 with the previously described features and functions including, but not limited to, shrinking of the reaction chamber 208, seating of the plunger 200 at the plunger seat 404 and the like the device is able to reconstitute a specified amount of reagent with 10 percent or better (e.g., 5 percent) precision. Stated another way, for a reagent preparation and dispensing device 100 configured to reconstitute 10 micro liters the device 100 is able to reconstitute the reagent with precision near plus or minus 1 micro liter (around a fortieth of a drop). In another example, the device 100 is configured to reconstitute 10 micro liters of a reagent with 5 percent precision, for instance plus or minus 0.5 micro liters or around eightieth of a drop).

Referring to FIG. 4B, addition of the solution 212 to the reaction chamber 208 to form the reagent solution by movement of the activator 106 and first plunger 200 displaces the gas in the reaction chamber 208 present before reconstitution of the reagent 204. The frangible tip 238 is coupled with the dispensing tip as previously described above. The frangible tip 238 allows for reconstitution of the reagent 204 within the reaction chamber 208 without undesirable dispensing of the partially reconstituted reagent. Provision of the frangible tip 238 further seals the reaction chamber 208 and prevents the release of gas through the dispensing tip 206 displaced by the addition of the solution 212.

A venting means including a vent path 408 is provided within the reagent preparation and dispensing device 100 to vent the gas displaced from the reaction chamber 208. The vent path 408 permits the displaced gas from the reaction chamber 208 to escape from the reaction chamber and exit the reagent preparation and dispensing device 100 without developing an overpressure within the reaction chamber that could prematurely dispense the reconstituted reagent through fracture of the frangible tip 238. Stated another way, pressurizing of the reaction chamber 208 is prevented by the vent path 408. As shown in the example provided in FIG. 4B, the vent path 408 extends through the reagent preparation and dispensing device 100 in a direction opposed to the frangible tip 238 and the dispensing tip 206 sized and shaped to pass the reconstituted reagent therethrough. By extending the vent path 408 in an opposed direction the reagent preparation and dispensing device 100 may be maintained in the substantially vertical orientation shown throughout operation of the device 100 to thereby allow the technician to simply operate the activator 106 without having to adjust the orientation of the reagent preparation and dispensing device 100 to ensure proper venting of the gas from the reaction chamber 208 while reconstituting the reagent 204. The venting means described herein includes the vent path 408 separately or together with the components of the device 100 forming the vent path. Optionally, the venting means includes one or more of the device components described herein forming the vent path 408.

Referring now to FIG. 4B, the vent path 408 begins in the reaction chamber 208 and extends through reaction chamber vents 410 formed in the dispensing tip 206. The vent path 408 extends from the reaction chamber vents 410 through the space formed between the barrel 104 and the dispensing tip 206. As shown in FIG. 4B, the vent path 408 continues along the dispensing tip 206 through the interconnecting gasket 228 to barrel passages 412 extending through the barrel 104 and into the barrel interior. Two barrel passages 412 are shown in FIG. 4B that extend through the barrel 104. In another example, one or more barrel passages extend through the barrel allowing the gas displaced from the reaction chamber 208 to vent from the reagent preparation and dispensing device 100 during addition of the solution 212 to the reaction chamber. For instance, as previously described, FIGS. 4A and 4B show two views of the reagent preparation and dispensing device 100. The view in 4B is rotated relative to the view in 4A and both views include barrel passages 412. By providing a plurality of barrel passages 412 through the barrel 104 gas displaced by the addition of the solution 212 to the reaction chamber 208 is easily able to pass through the barrel 104 and continue along the vent path 408.

In one example, as previously shown in FIG. 3B, the vent flange 306 engages with the interconnecting gasket 228 and substantially seals the vent path 408 from the reaction chamber 208 to the barrel passages 412. Sealing of the vent flange 306 at the interconnecting gasket 228 thereby substantially prevents the movement of gas displaced from the reaction chamber 208 into the region between the barrel 104 and body 102 and instead diverts the gas through the barrel passages 412 along the remainder of the vent path 408 where the gas can escape from the reagent preparation and dispensing device 100. Referring to FIG. 4C, In another example, a semi-permeable membrane 414 is positioned within the vent path 408. Optionally, the semi-permeable membrane 414 is positioned over the barrel passages 412 (e.g., on one or more of the interior or exterior of the barrel 104). The semi-permeable membrane 414 is configured to prevent the movement of the reagent mixture 400 from out of the device 100 through the vent path 408. For instance, the semi-permeable membrane 414 includes, but is not limited to, a hydrophobic membrane that permits the passage of gas, such as displaced gas from the reaction chamber 208 but prevents the passage of the reagent mixture 400. The reagent preparation and dispensing device 100 is thereby configured to retain the reagent mixture 400 within the device until dispensing of the mixture is desired while minimizing leaks of the mixture through the gas vent path 408. Optionally, the semi-permeable membrane 414 includes, but is not limited to, a lipophobic membrane, other membranes that facilitate passage of the flushing fluid and block passage of the reagent mixture, a suitable combination of membranes (e.g., lipophobic and hydrophobic) and the like.

Referring again to FIG. 4B, after passing through the barrel passages 412, the displaced gas moves through the barrel 104 and the space between the barrel interior and the first plunger 200. Because the second plunger gasket 222 is disengaged from the interior of the barrel 104 the vent path 408 continues uninterrupted along the second plunger 202 in between the activator 106 and the barrel 104. As previously described above, the activator 106 includes activator lugs 308 sized and shaped to engage with barrel stop 406 and slidably move within the first barrel slots 310 (and second barrel slots described below). The activator lugs 308 extend around only a portion of the activator 106 thereby allowing the gas vented along the vent path 408 to divert around the activator lungs 308 and continue on between the activator 106 and body 104 (e.g., for instance through the first barrel slots 310) to exit the reagent preparation and dispensing device 100.

The vent path 408 thereby provides for equalization of pressure within the reaction chamber 208 during reconstitution of the reagent 204 therein. The solution 212 is able to freely move into the reaction chamber 208 because the vent path 408 remains open throughout movement of the first plunger 200 relative to the barrel 104. Stated another way, because the vent path 408 remains open from a starting position of the first plunger 200 shown in FIG. 3B to a seated position shown in FIG. 4B gas displaced by the addition of the solution into the reaction chamber 208 is continuously vented from the reagent preparation and dispensing device 100 without pressurizing the reaction chamber 208. The solution 212 is thereby added to the reaction chamber 208 without any resistance from pressure developed within the reaction chamber 208. Further, the technician is able to perform the entire movement of the first plunger 200 to add the solution 212 to the reaction chamber 208 while maintaining the reaction preparation and dispensing device 100 in a single vertical orientation throughout reconstitution of the reagent 204.

Further still, referring again to FIG. 3B, because the first plunger gasket 220 is positioned below the barrel passages 412 the vent path 408 remains open throughout the entire movement of the first plunger 200 relative to the barrel 104. The vent path 408 is substantially isolated from the solution reservoir 214 and the reaction chamber 208 and only in communication with the reaction chamber 208 through the reaction chamber vents 410. The first plunger 200 is thereby able to freely translate from the position in FIG. 3B to the seated position shown in FIG. 4B thereby moving the entirety of the solution 212 into the reaction chamber 208 while venting displaced gas through the vent path 408. In contrast, if a vent was provided within the solution reservoir 214, after passage of the first plunger 200 past the vent, such a vent would be closed and gas displaced from the reaction chamber 208 would no longer be vented. The vent path 408 addresses this issue by providing an entirely separate path from the solution reservoir 214 throughout the entirety of the movement of the first plunger 200. As discussed above, gas displaced from the reaction chamber 208 by the addition of the solution 212 is thereby readily vented through the vent path 408 without pressurizing the reaction chamber 208.

As described above, the reagent preparation and dispensing device 100 is configured to consistently reconstitute precise small volumes of reagent (e.g., between 10 and 300 microliters with around 5 to 10 percent precision). The vent path 408 further facilitates the precise reconstitution of the reagent 204 at these volumes. By venting gas within the reaction chamber 208 as solution 212 is added back pressure is eliminated throughout the movement of the first plunger 200 and the full solution volume is delivered to the reaction chamber. Providing the vent path 408 ensures the first plunger 200 fully seats on the plunger seat 404 and substantially all of the solution 212 is correspondingly delivered from the solution reservoir 214 to the reaction chamber. Back pressure acting against the movement of the first plunger 200 is thereby eliminated. Further still, the vent path 408 substantially prevents the escape of the reconstituted reagent mixture 400, for instance through the vent path, because the vent path extends out of the top of the reaction chamber 208 relative to the dispensing tip 206 and the reagent is reconstituted at the bottom of the reaction chamber near the tip. Flipping of the reagent preparation and dispensing device 100 to reconstitute the reagent (for instance where gas is vented through the dispensing tip) is thereby avoided and the risk of a portion of the reagent mixture prematurely exiting through an orifice, such as the dispensing tip 206 is substantially avoided. In another example, The vent path 408 includes a semi-permeable membrane that further prevents unintended delivery of a portion of the reagent mixture 400 through the vent path prior to a desired delivery through the dispensing tip 206.

Figure 5A:
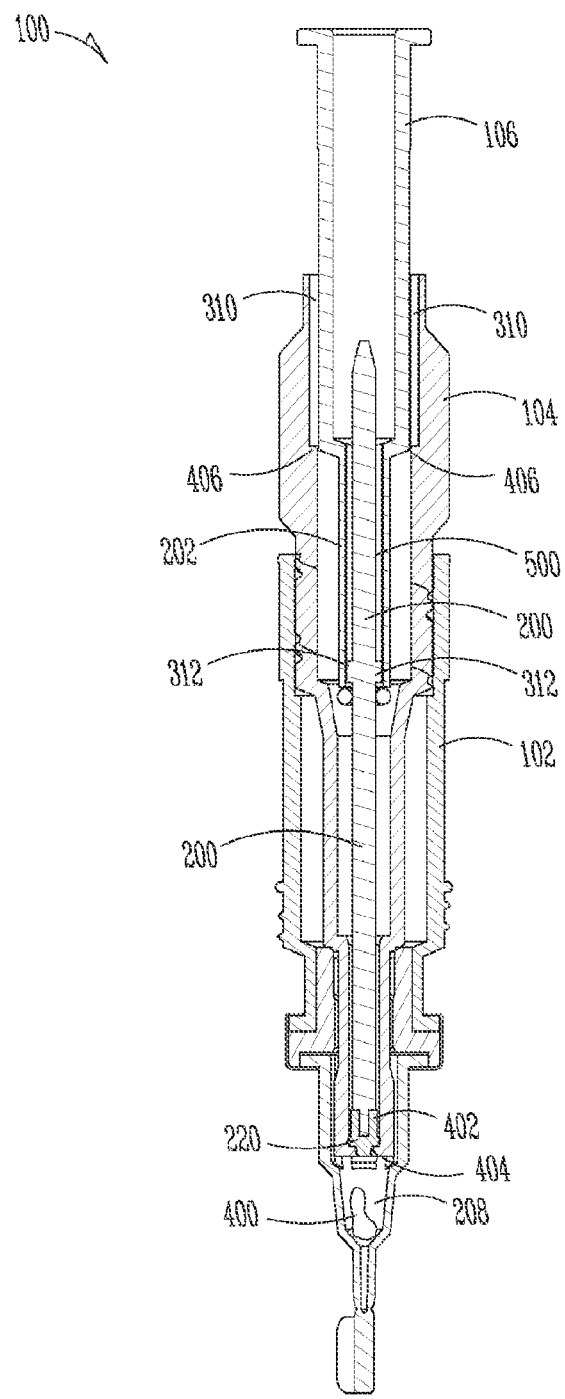
FIG. 5A is a cross sectional view of the device shown in FIG. 3A rotated to show the plunger lugs disengaged from the plunger stops and positioned within activator slots
Figure 5B:
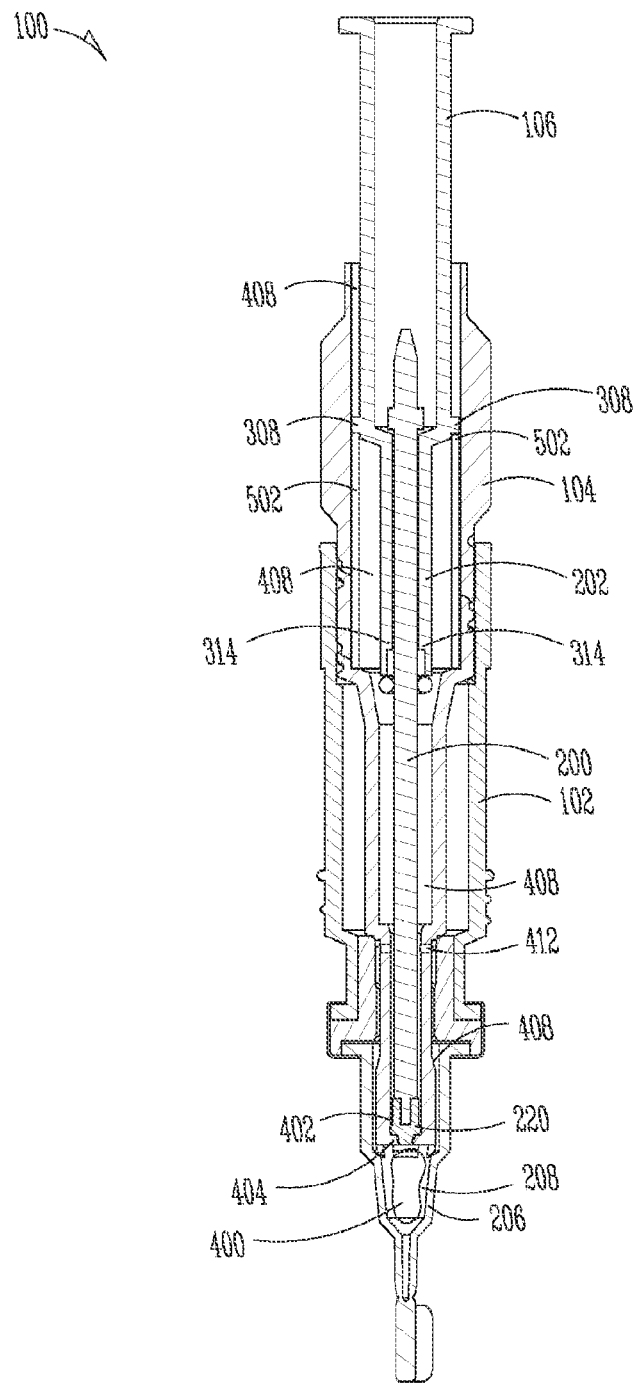
FIG. 5B is a cross sectional view of the device shown in FIG. 5A with activator lugs disengaged from barrel stops and positioned within second barrel slots.

FIGS. 5A and 5B show the reagent preparation and dispensing device 100 between the configurations shown in FIGS. 4A-C and FIGS. 6A, B (described below). Relative to FIGS. 4A-C the activator 106 of the reagent preparation and dispensing device 100 is rotated relative to the barrel 104 and the first plunger 200. As was previously shown and described in FIGS. 3A-C, engagement of the plunger lugs 312 with the activator stops 314 of the first plunger 200 and the activator 106, respectively, allows for the transmission of movement from the activator 106 to the plunger 200 for pushing of the solution 212 into the reaction chamber 208. After the addition of the solution 212 to the reaction chamber 208 for reconstitution of the reagent 204, the first plunger 200 including the first plunger gasket 220 is seated in the orientation shown in FIGS. 5A and 5B (as well as FIGS. 4A-C). Further movement of the first plunger 200 is arrested by the engagement of the activator lugs 308 with the barrel stop 406 and engagement of the plunger flange 402 with the plunger seat 404. After the addition of the solution 212 to form the reagent mixture 400, additional movement of the activator 106 is needed to dispense the reagent mixture from the reagent preparation and dispensing device 100. To facilitate movement of the activator 106 relative to the seated first plunger 200, the activator 106 is rotated relative to the first plunger 200 as well as the barrel 104. Rotation of the activator 106 moves the activator stops 314 out of phase with the plunger lugs 312. As shown in FIG. 5A, the plunger lugs 312 are positioned within plunger slots 500 of the activator 106 (and the second plunger 202).

Referring now to FIG. 5B, rotation of the activator 106 relative to the barrel 104 also positions the activator lugs 308 out of phase with the barrel stop 406 shown in FIG. 5A. The activator lugs 308 are instead positioned in second barrel slots 502 extending toward the dispensing tip 206 to allow for additional movement of the activator 106 relative to the barrel 104. Referring to both FIGS. 5A and 5B, disengagement of the plunger lugs 312 and activator lugs 308 frees the activator 106, including the second plunger 202, to move relative to the barrel 104 and the first plunger 200. As will be described in further detail below, movement of the activator 106 and the second plunger 202 relative to the first plunger 200 and the barrel 104 closes the vent path 408 and forms a flushing fluid chamber within the reagent preparation and dispensing device 100. Further, movement of the activator 106 and the second plunger 202 moves flushing fluid from the flushing gas chamber into the reaction chamber 208 for dispensing of the reagent mixture 400 through the dispensing tip 206.

Figure 6A:
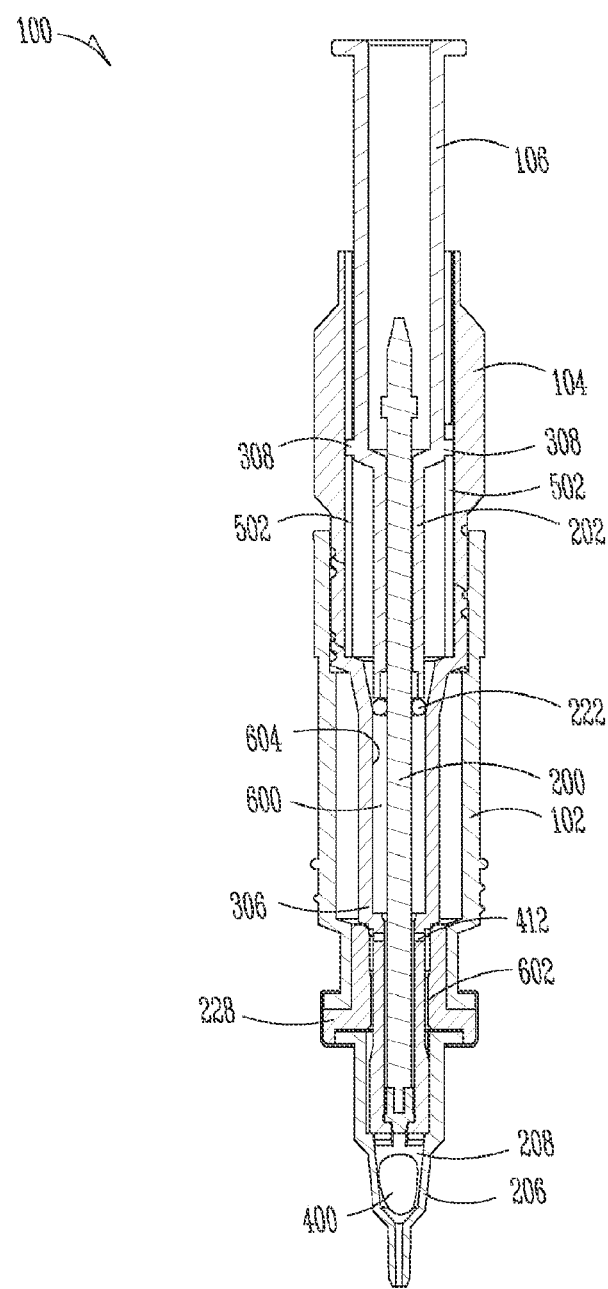
FIG. 6A is a cross sectional view of the device shown in FIG. 3A as the activator and a second plunger are depressed.
Figure 6B:
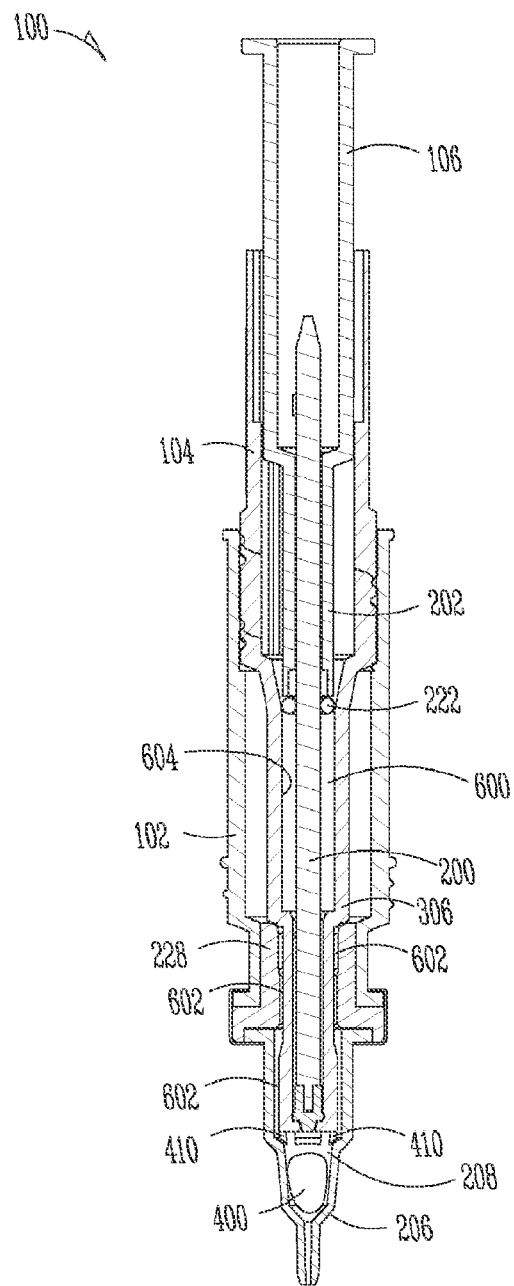
FIG. 6B is a cross sectional view of the device shown in FIG. 5A rotated 90 degrees about the device longitudinal axis.
Figure 7:
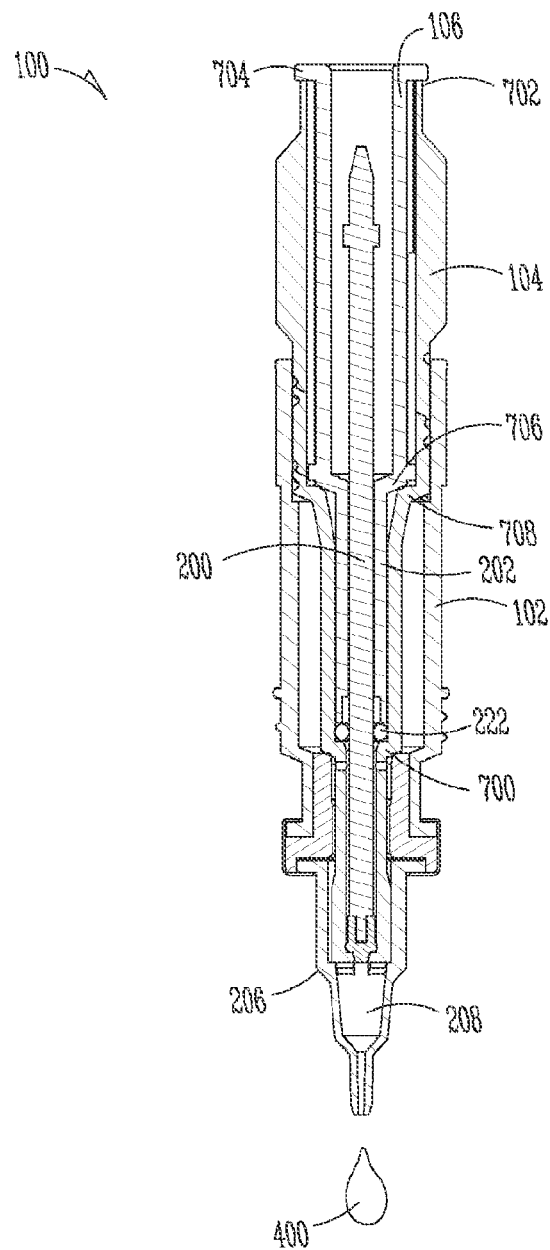
FIG. 7 is a cross sectional view of the device shown in FIG. 3A with the reagent mixture dispensed.

FIGS. 6A and 6B show the reagent preparation and dispensing device 100 as the activator 106 and the second plunger 202 are transitioning from the orientation shown in FIGS. 4A-C to a fully dispensed configuration shown in FIG. 7. As previously described, with the activator 106 rotated relative to the first plunger 200 and the barrel 104 the activator 106 and the second plunger 202 are movable relative to these features to dispense the reagent mixture 400 from the dispensing tip 206. As shown in FIG. 6A, for example, the activator lugs 308 are positioned within the second barrel slots 502, and as shown in FIG. 5A the plunger lugs 312 are slidably received within the plunger slots 500 thereby permitting the second plunger 200 and the activator 106 to slide along the first plunger 200. As the second plunger 202 is advanced along the first plunger 200 the second plunger gasket 222 engages with a barrel inner wall 604. Engagement of the second plunger 202 including the second plunger gasket 222 with the barrel inner wall 604 (e.g., a vent wall) seals the vent path 408 shown in FIGS. 4A-C and prevents the continued flow of gas from the reaction chamber 208 through the vent path 408. With the vent path 408 in this closed configuration, a flushing fluid chamber 600 (a flushing means or part of a flushing means) is formed by the second plunger 202 and the barrel 104. Continuing movement of the activator 106 and the second plunger 202 pressurizes the reaction chamber 208 and pushes a flushing fluid, such as air, through the flushing fluid chamber 600 and into the reaction chamber 208 for dispensing of the reagent mixture 400 through the dispensing tip 206. As shown in FIGS. 6A, B, because the device 100 is oriented vertically during reconstitution the reagent mixture 400 settles into the funnel of the reaction chamber 208 adjacent to the dispensing tip 206. The flushing fluid delivered to the reaction chamber at the opposed end from the tip 206 thereby flushes the reagent mixture 400 through the funneled reaction chamber and out of the tip.

Referring first to FIG. 6A, the flushing fluid chamber 600 is shown in communication with the reaction chamber 208 through a flushing path 602 extending therebetween. The flushing means described herein includes one or more of the flushing path 602, the vent path 408, the flushing fluid chamber 600 separately or together. Optionally, the flushing means includes one or more of the device 100 components described herein forming the vent path 602 and the flushing fluid chamber 600.

The flushing path 602 in the example shown in FIGS. 6A and 6B uses the same route as the vent path 408 previously described (e.g., the vent path extends through the flushing fluid chamber 600). For instance, the flushing path 602 begins at the flushing fluid chamber 600 and extends through the barrel passages 412 formed in the barrel 104. The flushing path 602 extends along the barrel 104 and the interconnecting gasket 228 as well as the dispensing tip 206 on its way toward the reaction chamber 208. Referring next to FIG. 6B, the flushing path 602 continues along the barrel 104 and extends into the reaction chamber 208 through the reaction chamber vents 410. Movement of the flushing fluid into the reaction chamber 208 along the flushing path 602 correspondingly pushes the reagent mixture 400 through the dispensing tip 206 and allows for complete dispensing of the reagent mixture from the reagent preparation and dispensing device 100.

In one example, as with the vent path 408, described above, the engagement of the vent flange 306 with the interconnecting gasket 228 ensures the flushing fluid moving from the flushing fluid chamber 600 through the flushing path 602 is directed toward the reaction chamber 208 during movement of the second plunger 202. Stated another way, the engagement of the vent flange 306 with the interconnecting gasket 228 seals the flushing path 602 thereby preventing leaks of flushing fluid and ensuring the flushing fluid is transmitted directly to the reaction chamber 208 for dispensing of the reagent mixture 400.

Actual physical engagement between the second plunger 208 and the reagent mixture 400 is not needed to dispense the reagent mixture from the reagent preparation and dispensing device 100. Instead, the flushing fluid chamber 600 includes a sufficient amount of flushing gas (or another fluid configured for flushing the reagent mixture 400) through the dimensioning of the volume of the chamber to enable the full dispensing of the reagent mixture 400 through the depression of the activator 106 and corresponding movement of flushing fluid through the flushing passage 602 into the reaction chamber 208. In one example, the flushing fluid chamber 600 has a volume greater than the volume of the reaction chamber 208. The larger volume of the flushing fluid chamber 600 ensures a correspondingly large volume of flushing fluid is pushed into the reaction chamber 208 to fully dispense the reagent mixture 400 from the dispensing tip 206. Stated another way, the relatively large volume of flushing fluid within the flushing fluid chamber 600 continues to stream into the reaction chamber 208 throughout the movement of the second plunger 202 thereby ensuring the reagent mixture 400 is flushed out of the dispensing tip 206 with a relatively larger volume of fluid. Because physical engagement between the second plunger and 202 and the reagent mixture 400 is not used to dispense the mixture from the dispensing tip 206, movement of the second plunger 202 through a larger volume (e.g., the volume of the flushing fluid chamber 600) is thereby able to push a correspondingly larger volume of fluid into the relatively small reaction chamber 208 to ensure the complete dispensing of the reagent mixture 400 through the dispensing tip 206. By using the larger volume of flushing from the flushing fluid chamber 600 the entire amount of the reconstituted reagent mixtures is thereby dispensed, and remaining reagent residue on the interior of the dispensing tip 206 is substantially prevented.

The combination of features described herein, including but not limited to shrinking of the reaction chamber 208, seating of the first plunger 200 at the plunger seat 404 to substantially eliminate the solution reservoir 214, provision of the vent path 408 and the like ensure the consistent and precise reconstitution of the reagent mixture at micro liter scale volumes (e.g., from 10 to 300 microliters). The flushing fluid chamber 600 and the flushing passage 602 (including in one example the vent path 408) cooperate with these previously described features to ensure substantially all of the reconstituted reagent mixture 400 is dispensed from the device 100. In one example, the flushing fluid chamber 600 and the flushing passage 602 alone or in combination with the other recited features described herein ensure around 80 percent of the reconstituted reagent mixture 400 is precisely and consistently dispensed from the device 100 (e.g., 80 percent or better of a quarter of a drop or 10 micro liters). In another example, the flushing fluid chamber 600 and the flushing passage 602 alone or in combination with the other recited features described herein ensure around 90 percent of the reconstituted reagent mixture 400 is precisely and consistently dispensed from the device 100. These features and functions mitigate the need in other devices to reconstitute large volumes of reagent, for instance 300 micro liters, a milliliter or more, and then dispense only a specified portion of the reconstituted reagent. Many reagents are costly and the reconstitution of large volumes of the reagent and subsequent dispensing of only a portion of the reagent makes these other devices cost prohibitive and impractical. The reagent preparation and dispensing device 100 reconstitutes only the amount of reagent needed (e.g., expensive reagents or reagents with short shelf lives) for the particular application at a micro liter scale and is able to deliver substantially all of the reconstituted reagent.

FIG. 7 shows the reagent preparation and dispensing device 100 in the fully dispensed configuration with the activator 106 and the second plunger 202 fully received within the barrel 104 and the reagent mixture 400 is dispensed from the dispensing tip 206. As previously described above, movement of the activator 106 and the second plunger 202 relative to the barrel 104 forces fluid within the flushing fluid chamber 600 through the flushing path 602 into the reaction chamber 208 to dispense the reagent mixture 400. When the flushing fluid is fully moved out of the flushing fluid chamber 600 the second plunger 202 including the second plunger gasket 222 is fully seated within the barrel 104 as shown in FIG. 7. For instance, the second plunger gasket 222 is engaged with a second plunger seat 700. In another example, a first activator flange 704 at an opposed end of the activator 106 from the second plunger 202 is engaged against a second barrel stop 702 formed in the barrel 104. In still another example, the reagent preparation and dispensing device 100 includes a second activator flange 706 on the activator 106. The second activator flange 706 is sized and shaped to engage with the second barrel stop 708 on the barrel 104 after the activator 106 is fully moved to force the flushing fluid into the reaction chamber 208. The barrel 104, the activator 106 and the second plunger 202 are sized and shaped to ensure that full movement of the activator 106 and second plunger 202 into the barrel 104 fully pushes the volume of flushing fluid within the flushing fluid chamber 600 into the reaction chamber 208. After engagement of the second plunger gasket 222, the first activator flange 704 and the second activator flange 706 with corresponding stops and seats 700, 702, 708 the technician is affirmatively aware the reagent mixture 400 is fully dispensed from the reagent preparation and dispensing device 100 because the activator 106 is fully engaged and further movement of the activator 106 into the device 100 is substantially prevented. By tactile sensation, e.g., arresting of further movement, the technician is confident that the full amount of the reagent mixture 400 is dispensed from the reagent preparation and dispensing device.

Figure 8A:
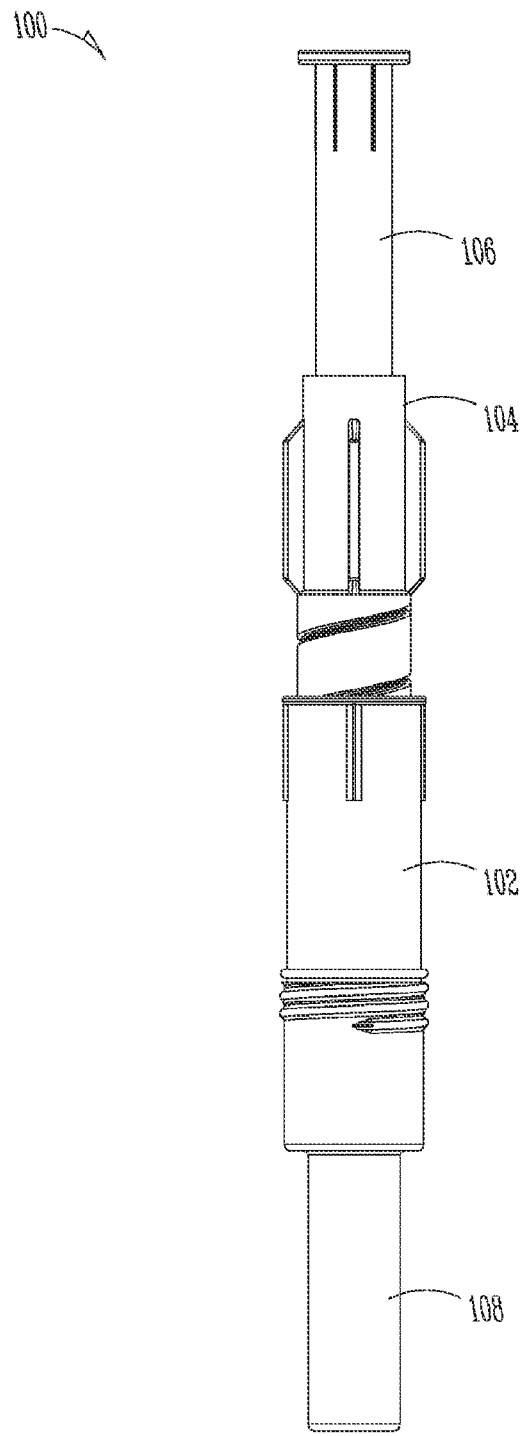
FIG. 8A is a side view of the device shown in FIG. 2A in an as-supplied configuration.

FIGS. 8A through 8F show the reagent preparation and dispensing device 100 in the configurations for reconstitution and dispensing of a reagent mixture as previously described and shown in FIGS. 2A through 7. Referring first to FIG. 8A, the reagent preparation and dispensing device 100 is shown in a starting orientation with the activator 106 extending out of the barrel 104 and the barrel 104 is rotatably coupled with the body 102. In the starting orientation the barrel 104 is in this orientation with a reservoir seal 226 interposed between the reagent reservoir 210 and the solution reservoir 214 (see FIG. 2A). A dispensing tip 206 including the reagent reservoir 210 having the reagent 204 therein is held within a cap 108. The cap 108 includes, in one example, a desiccant 216 that cooperates with the frangible tip 238 to substantially prevent the ingress of moisture into the reagent reservoir 210. Undesired reconstitution of the reagent 204 prior to piercing of the reservoir seal 226 is thereby prevented.

Figure 8B:
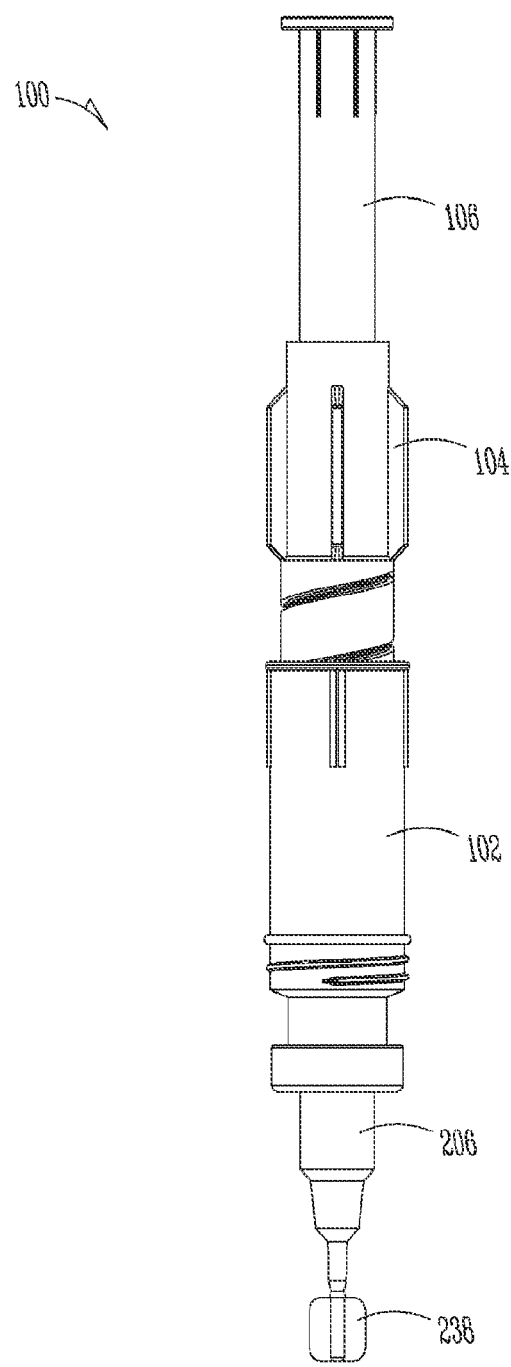
FIG. 8B is a side view of the device shown in FIG. 2A with a storage cap removed.

Referring now to FIG. 8B, the cap 108 is removed exposing the dispensing tip 206 and the frangible tip 238 of the reagent preparation and dispensing device 100. As shown, the activator 106 remains in the starting orientation as does the barrel 104 relative to the body 102. In another example, the cap 108 remains on the dispensing tip 206 throughout reconstitution until removal of the frangible tip 238 is required for dispensing.

Figure 8C:
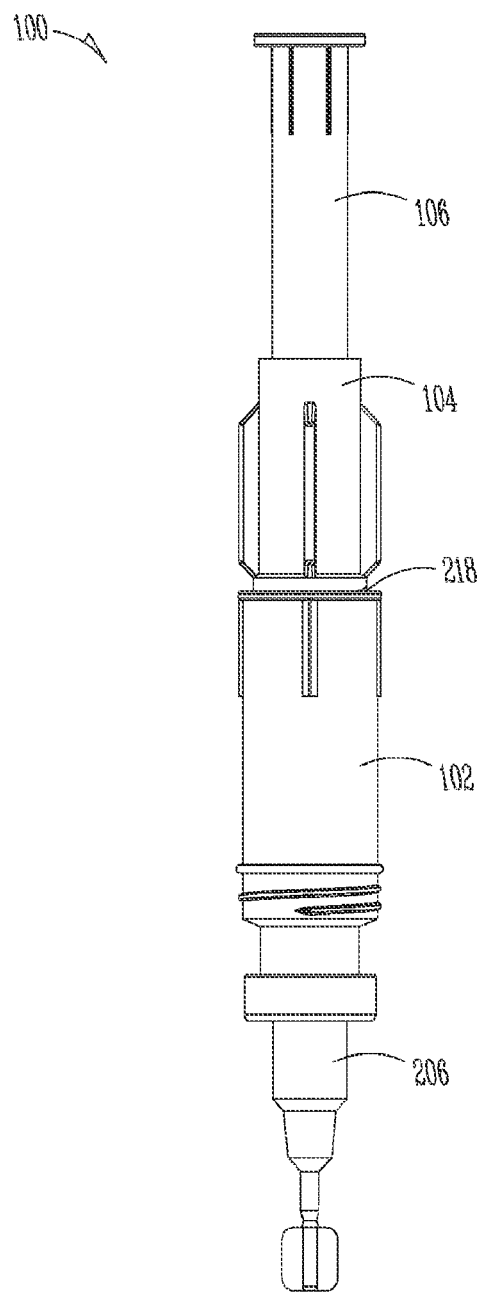
FIG. 8C is a side view of the device shown in FIG. 3A with a barrel moved to open a reaction chamber including a reagent.

FIG. 8C shows the reagent preparation and dispensing device 100 in a first intermediate configuration. The barrel 104 is moved relative to the body 102 as shown in FIGS. 3A-C. Movement of the barrel 104 relative to the body 102 moves the piercing surface 236 of the barrel 104 through the reservoir seal 226 (see FIG. 2A). Piercing of the reservoir seal 226 allows the solution reservoir 214 to communicate with the reaction chamber 208 including the reagent 204. As previously described, movement of the barrel 104 fills the space within the reagent reservoir 210 leaving the reaction chamber 208 with a smaller volume with the reagent 204 therein.

Referring again to FIG. 8C, the reagent preparation and dispensing device 100, in one example, includes a mechanical fitting 218 sized and shaped to translate rotation of the barrel 104 into longitudinal movement of the barrel relative to the body 102. For instance, in one example, a mechanical fitting 218 includes threading on the opposed surfaces of the barrel 104 and the body 102. Rotation of the barrel 104 thereby longitudinally moves the barrel 104 into the body 102. The piercing surface 236, as previously described, is driven through the reservoir seal 226. In other examples, the barrel 104 is slidably coupled with the body 102 and the mechanical fitting 218 facilitates the slidable coupling therebetween. Longitudinal movement of the barrel 104, for instance, by depression from the user is used to move the piercing surface 236 through the reservoir seal 226.

Figure 8D:
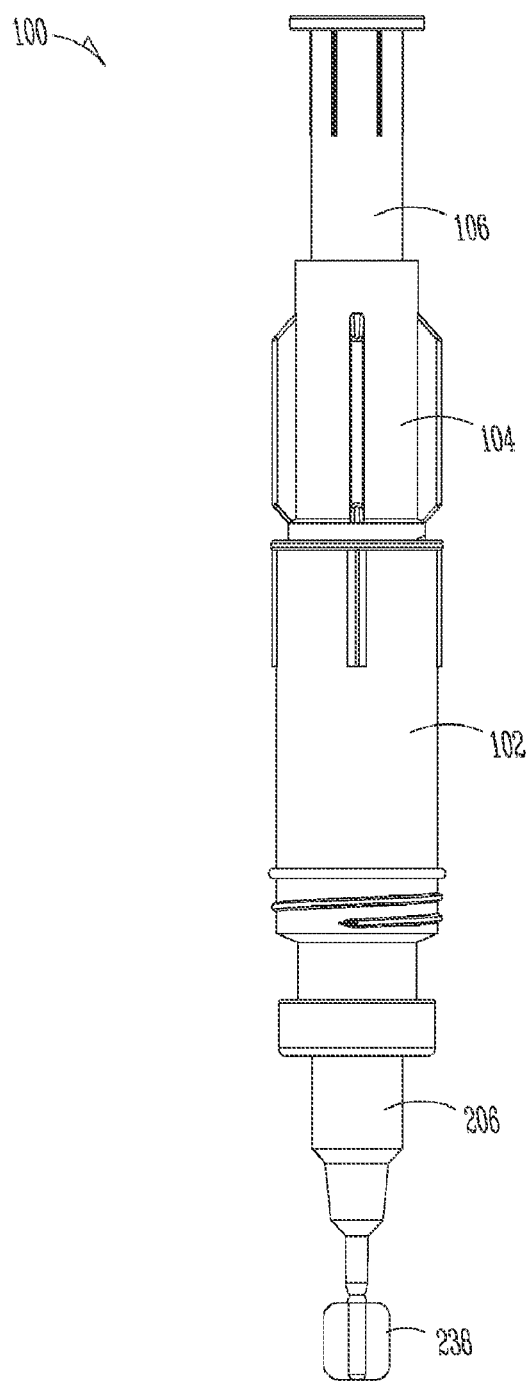
FIG. 8D is a side view of the device shown in FIG. 4A with an activator and a first plunger depressed to reconstitute a reagent.

Referring now to FIG. 8D, the reagent preparation and dispensing device 100 is shown in a second intermediate configuration with the activator 106 depressed relative to the orientation shown in FIG. 8C. The activator 106 is depressed at least partially into the barrel 104. As shown in FIGS. 4A-C, movement of the activator 106 drives the first plunger 200 through the barrel 104. Movement of the first plunger 200 correspondingly moves the solution 212 out of the solution reservoir 214 (see FIGS. 3A-C) and into the reaction chamber 208 containing the reagent 204. Movement of the first plunger 200 thereby reconstitutes the reagent 204 by adding the solution 212 to the reagent 204. Addition of the solution to the reagent 204 forms the reagent mixture 400 shown in FIGS. 4A-C. As shown in FIGS. 4B and 4C, the activator 106 and the first plunger 200 move as an assembly into the configuration shown in FIGS. 4B and 4C until the plunger flange 402 of the first plunger 200 engages with and seats on the plunger seat 404. Further, in another example, movement of the activator 106 and first plunger 200 is also arrested by engagement of activator lugs 308 with a barrel stop 406 formed in the barrel 104. Engagement of these features provides an affirmative notification to the technician that the solution 212 previously in the solution reservoir 214 is fully dispensed into the reaction chamber 208 by movement of the activator 106. Stated another way, as the activator 106 is engaged against the features within the barrel, including the barrel stop 406 and the plunger flange 402, the first plunger 200 has moved through the entirety of the solution reservoir 214 and has thereby fully dispensed the solution 212 into the reaction chamber 208 for reconstitution.

Figure 8E:
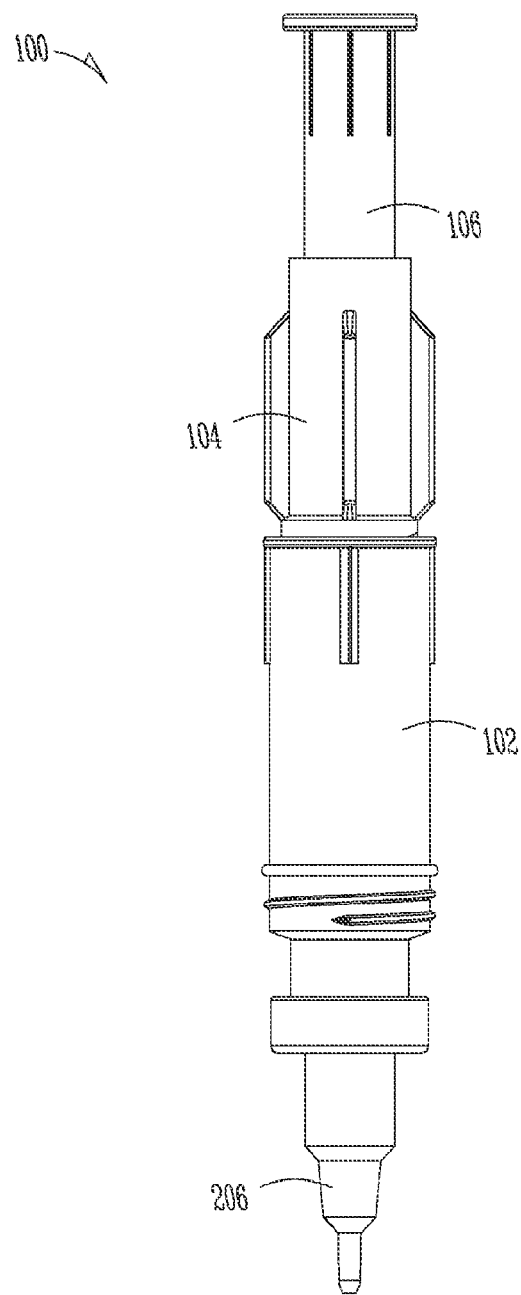
FIG. 8E is a side view of the device shown in FIG. 4A with a frangible tip of a dispensing tip removed.

As shown in FIG. 8E, the frangible tip 238 is removed from the dispensing tip 206 in preparation for dispensing of the reagent mixture 400 from the device 100. In the example shown, the activator 106 is rotated relative to the barrel 104. As previously described and shown in FIGS. 6A, B, rotation of the activator 106 positions the activator lugs 308 within the second barrel slots 502. Positioning the activator lugs 308 within the second barrel slots 502 permits further longitudinal movement of the activator 106 relative to the barrel 104 and the body 102. Additionally, rotation of the activator 106 disengages the plunger lugs 312 from the activator stops 314 and positions the lugs within the plunger slots 500. The activator 106 is thereby unlocked from the first plunger 200 and configured for longitudinal movement relative to the first plunger 200 as well as the barrel 104. In the configuration shown in FIGS. 6A, B and 8E, continued longitudinal movement of the activator 106 relative to the barrel 104 dispenses the reagent mixture, as described above and further described below.

Figure 8F:
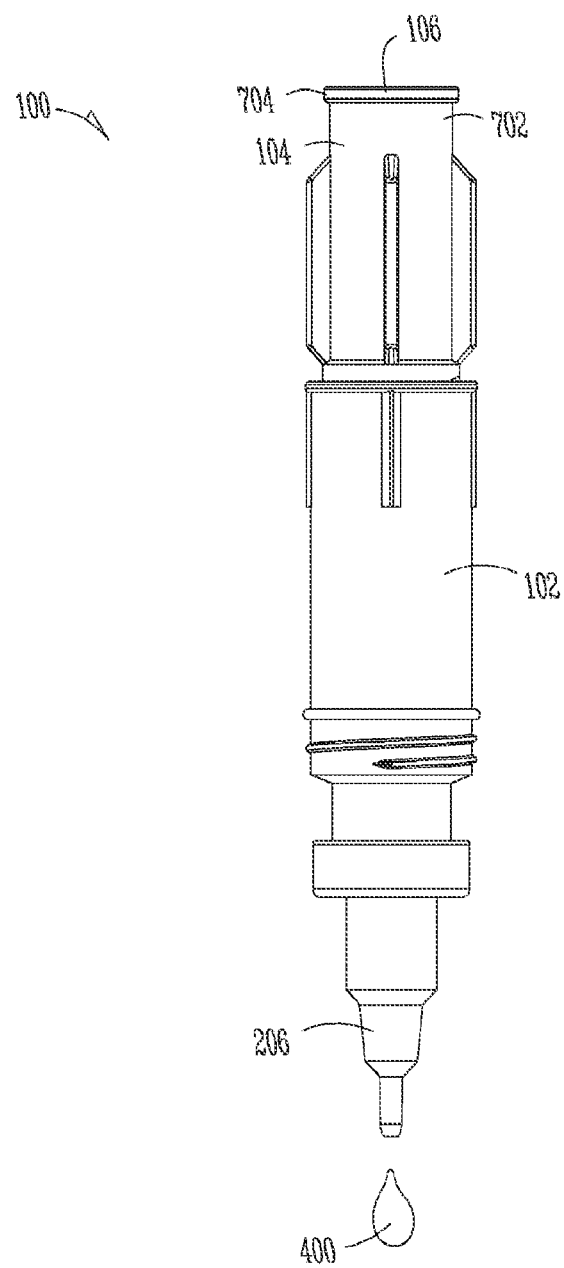
FIG. 8F is a side view of the device shown in FIG. 7 with an activator and a second plunger depressed to dispense the reagent mixture.

Once the frangible tip 238 is removed from the dispensing tip 206 the reagent preparation and dispensing device 100 is in a configuration ready to dispense the reagent mixture 400. Referring to FIG. 8F, the reagent preparation and dispensing device 100 is shown in a dispensing configuration with the activator 106 depressed relative to the barrel 104. As shown, the activator 106 is moved from a configuration shown in FIG. 8E to that shown in 8F. Referring to FIGS. 6A and 6B, the reagent preparation and dispensing device 100 is shown in a configuration with the activator 106 between the orientations shown in FIGS. 8E and 8F. The activator 106 is moved into the barrel 104 relative to the barrel 104 and the first plunger 200. The second plunger 202 including the second plunger gasket 222 is engaged with the barrel inner wall 604. Engagement of the second plunger 202 (including, in one example, the second plunger gasket 222) with the barrel inner wall 604 seals the vent path 408 and prevents the venting of gases from the reaction chamber 208 out of the reagent preparation and dispensing device 100. In contrast, the vent path 408 is shown in the preceding open configuration in FIGS. 4A, B.

Once the vent path 408 is closed by the engagement of the second plunger 202 with the barrel 104 a flushing fluid chamber 600 is formed. As shown in FIGS. 6A and 6B, the flushing fluid chamber 600 is formed by the second plunger 202 engaged with the barrel inner wall 604. The flushing fluid chamber 600 communicates with the reaction chamber 208 through the flushing path 602. As shown in FIG. 6A, the flushing path 602 travels through the reagent preparation and dispensing device 100 in a similar manner to the vent path 408 shown in FIG. 5B. For instance, the flushing path 602 extends through the barrel passages 412 along the barrel 104 between the interconnecting gasket 228. The flushing path 602 extends into the reaction chamber 208 through the reaction chamber vents 410 positioned around at least a portion of the dispensing tip 206. As the activator 106 including the second plunger 202 is moved longitudinally relative to the barrel 104 the flushing fluid (e.g., air, an inert gas, a fluid immiscible with the reagent mixture 400 and the like) within the flushing fluid chamber 600 is pushed out of the flushing fluid chamber 600 and through the flushing path 602 into the reaction chamber 208. Delivery of the flushing fluid into the reaction chamber 208 pushes the reagent mixture 400 out of the dispensing tip 206.

In one example, the flushing fluid chamber 600 includes a volume in the orientation shown in FIGS. 6A and 6B greater than the volume of the reaction chamber 208. For instance, the reaction chamber 208 is included in the reagent reservoir 210 shown in FIG. 2A. Movement of the barrel 104 into the reagent reservoir 210 shrinks the reagent reservoir leaving only the reaction chamber 208 with the reagent 204 and later the reagent mixture 400 therein. Shrinking the volume of the reagent reservoir 210 to that of the reaction chamber 208 ensures the greater volume of flushing fluid from the flushing fluid chamber 600 fully dispenses the reagent mixture 400 from the dispensing tip 206. Stated another way, because the flushing fluid within the flushing fluid chamber 600 includes a greater volume than the reaction chamber 208 movement of the activator 106 and the second plunger 202 provides a steady stream of flushing fluid to the small volume of the reaction chamber 208 that reliably pushes the reagent mixture 400 from the dispensing tip 206 and continues to flush any residue of the reagent mixture 400 from the reaction chamber 208 until the second plunger 202 is fully translated through the flushing fluid chamber 600.

Referring now to FIG. 7, once the activator 106 is fully moved relative to the barrel 104 the first activator flange 704 is engaged with the second barrel stop 702. Additionally, in another example, the second plunger 202 including the second plunger gasket 222, is engaged with the first barrel stop 700 formed in the barrel 104. Engagement of the flange 704 and the second plunger 202 with the corresponding stops provides an affirmative notification to the technician that the flushing fluid from the flushing chamber 600 is fully pushed through the reaction chamber 208 and the reagent mixture 400 is thereby fully dispensed from the device 100. That is to say, full translation of the activator 106 relative to the barrel 104 is configured to dispense the entire amount of reagent mixture 400 from the dispensing tip 206 while providing an affirmative notification to the technician that the reagent mixture 400 is dispensed without residue within the reaction chamber 208.

Figure 9:
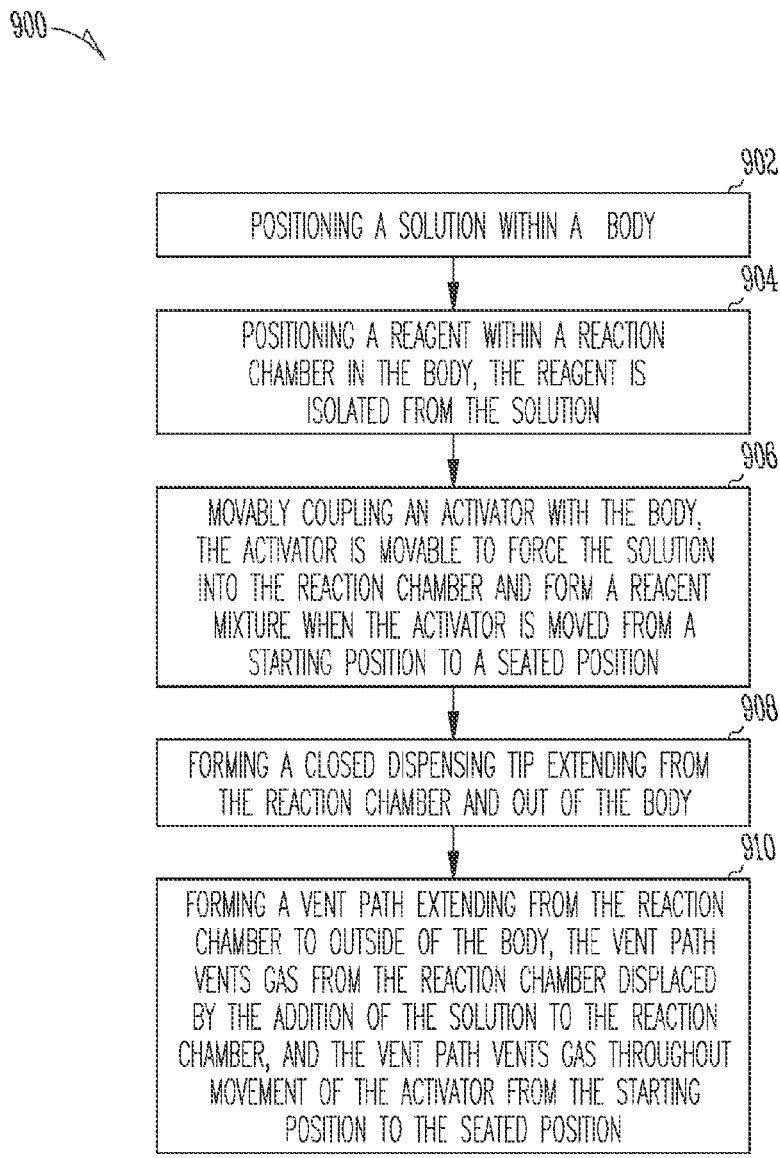
FIG. 9 is a block diagram showing one example of a method for making a reagent preparation and dispensing device.

FIG. 9 shows one example of a method 900 for making a reagent preparation and dispensing device such as the reagent preparation and dispensing device 100 shown in FIG. 2A. Reference is made in the description of the method 900 to elements, features and the like described previously herein. Where reference is made to a numbered element or other feature the reference is not limiting but instead includes similar elements described herein as well as their equivalents.

At 902, the method 900 includes positioning a solution, such as the solution 212 shown in FIG. 2A, within a body 102. As shown in FIG. 2A, the solution 212, in one example, is positioned within a solution reservoir 214 within a barrel 104 movably coupled within the body 102. As further shown in FIG. 2A, the solution reservoir 214 formed by an interior surface of the barrel 104 and a first plunger 200 positioned within the barrel 104. As will be described in further detail below, the solution reservoir 214 is further sealed by a reservoir seal 226 interposed between the solution reservoir 212 and the reagent 204.

At 904, a reagent 204 is positioned within a reaction chamber 208 in the body 102. The reagent 204 is isolated from the solution 212 in the as delivered configuration (See FIG. 2A). In one example, a reservoir seal 226 is positioned between the solution reservoir 214 and the reagent reservoir 210 containing the reagent 204, as will be described in further detail below. The body 102, in one example, is intended to include the dispensing tip 206 shown in FIG. 2A. In another example, the dispensing tip 206 including the reagent reservoir 210 and the reagent 204 are considered separate components from the body 102.

At 906, an activator 106 is movably coupled with the body 102. The activator 106 is movable to force the solution 212 into the reaction chamber 208 and form a reagent mixture, such as the reagent mixture 400 shown in FIG. 4A. In one example, the activator 106 is selectively coupled with a first plunger 200. Movement of the activator 106 is transmitted to the first plunger 200 to force the solution 212 into the reaction chamber 208. As was described above, in one example, lugs and stops on one or more of the activator 106 and the first plunger 200 facilitate selective engagement between the activator and the first plunger 200. During the reconstitution and dispensing process the activator 106 is selectively engaged and disengaged from the first plunger 200 to add the solution to the reaction chamber 208 to form the reagent mixture 400 and later dispense the reagent mixture 400 from the dispensing tip 206.

At 908, a closed dispensing tip 206 (see FIG. 2A) is formed extending from the reaction chamber 208 out of the body 102. As shown in FIG. 2A, the dispensing tip 206, in one example, includes the reaction chamber 208 and the remainder of the dispensing tip 206 extends away from the reaction chamber 208 toward a frangible tip 238. In another example, the frangible tip 238 shown in FIGS. 2A and 2B closes the dispensing tip 206 prior to dispensing of the reagent mixture 400 (see FIG. 4A) from the reagent preparation and dispensing device 100. Optionally, the frangible tip 238 cooperates with the reservoir seal 226 to close the dispensing tip 206 having the reagent reservoir 210 (including the reaction chamber 208 and reagent 204) from the environment exterior to the device 100. Isolating the reagent reservoir 210 and the reagent 204 from the exterior environment substantially prevents the ingress of moisture into the reagent reservoir 210 and thereby prevents undesired premature reconstitution of the reagent 204.

In 910, a vent path 408 is formed within the reagent preparation and dispensing device 100. The vent path 408 extends from the reaction chamber 208 to outside of the body 102. The vent path 408 vents gas from the reaction chamber 208 displaced by the addition of the solution 212 to the reaction chamber. In one example, the vent path 408 vents gas and continues to vent gas from the reaction chamber throughout movement of the activator 106 from a starting position (see FIGS. 3A, 3B) to a seated position, such as the seated position shown in FIGS. 4A and 4B. Stated another way, the vent path 408 remains open throughout the entire range of travel of the first plunger 200. By maintaining the vent path 408 in an open configuration throughout the range of travel of the first plunger 200 gas is continuously vented from the reaction chamber 208 thereby allowing for the full addition of the solution 212 to the reaction chamber. Pressurization and over pressure within the reaction chamber 208 capable of resisting the movement of the activator 106 and the selectively coupled first plunger 200 are thereby substantially avoided allowing for the full addition of the solution to the reaction chamber 208 without opposition due to the over pressure.

Several options for the method 900 follow. In one example, the method 900 includes movably coupling a barrel, such as barrel 104, with the body 102. In one example, the barrel 104 is coupled with the body 102 through a mechanical fitting 218 interposed therebetween. For instance, surfaces of the barrel 104 and opposed surfaces of the body 102 include threading sized and shaped to rotatably engage the barrel 104 with the body 102. Rotation of the barrel 104 relative to the body 102 longitudinally moves the barrel 104 as well as the activator 106 and first plunger 200 positioned within the barrel 104. The activator 106, first plunger 200 and the barrel 104 thereby move as a single assembly relative to the body 102 as the barrel 104 is moved longitudinally relative to the body 102.

In another example, forming the vent path 408 includes extending the vent path between the barrel 104 and the body 102. As shown, for instance in FIG. 4B, the vent path 408 extends from the reaction chamber 208 through reaction chamber vents 410 formed between the dispensing tip 206 and the barrel 104. The vent path 408 continues along the barrel 104 and reaches the barrel passages 412. The barrel passages 412 extend through the barrel 104 and into the interior of the barrel adjacent to the first plunger 200. The vent path 408 thereafter continues along the first plunger 200 and extends between the first plunger 200 and the barrel inner wall 604 (e.g., a vent wall). The vent path 408 continues on past the second plunger 202 including, in one example, a second plunger gasket 222. As shown, the vent path 408 continues to extend through the barrel 104 along the barrel inner wall (e.g., vent wall) past activator lugs 308 and out of the barrel 104. In one example, a first portion of the vent path 408 includes the portion of the vent path extending from the reaction chamber 208 along an exterior of the barrel 104 to the barrel passages 412. A second portion of the vent path 408 extends through the interior of the barrel 104 between the inner barrel wall 604 and the first plunger 200. In another option, the second portion of the vent path 408 continues through the interior of the barrel 408 along the barrel inner wall 604 and the second plunger 202 and activator 106.

In another example, forming the vent path 408 includes forming the vent path through the body 102 from a reaction chamber 208. Further, forming the closed dispensing tip 206 includes forming a closed dispensing tip extending from the reaction chamber 208 in a direction opposed to the direction of the vent path 408. In still another example, forming the closed dispensing tip 206 includes extending the closed dispensing tip 206 from a first portion of the reaction chamber 208 such as a bottom most portion of the reaction chamber. Forming the vent path 408 includes extending the vent path 408 from a second portion of the reaction chamber (e.g., an upper portion) opposed to the first portion of the reaction chamber 208. By orienting the vent path 408 relative to the dispensing tip 206 the reagent preparation and dispensing device 100 is maintained in a single orientation such as a vertical orientation throughout the reconstitution and dispensing procedure. Rotation of the device 100, for instance, rotating the device into an orientation with the dispensing tip 206 oriented up and the activator 106 oriented down to vent gases from the reaction chamber is thereby avoided.

The vent path 408 facilitates the continued addition of solution to the reaction chamber 208 despite the closed dispensing tip 206. That is to say, while the dispensing tip 206 is closed (e.g., with the frangible tip) the vent path 408 vents gases displaced from the reaction chamber 208 by the addition of solution 212. The solution 212 is added to the reaction chamber 208 without developing an over pressure within the reaction chamber capable of opening the dispensing tip and dispensing the reagent mixture 408 prior to full reconstitution. Further, the first plunger 200 encounters no resistance from pressurization while pushing the solution 212 because the gas within the reaction chamber is vented.

In yet another example, the method 900 further includes forming a flushing chamber 600 within the body 102. For instance, as shown in FIG. 6A the flushing chamber 600 is formed within the body 102 between the barrel 104 and the first plunger 200. The flushing chamber 600 includes a flushing fluid in fluid communication with the reaction chamber 208 through the vent path 408 (e.g., the flushing path 602). In one example, the vent path 408, at least in part, becomes the flushing path 602 after closing of the vent path 408 through engagement of the second plunger 208 with the interior of the barrel 104. In another example, the method 900 includes movably coupling a second plunger 202 with the body 104 (e.g., the barrel 104) and the second plunger is operable to close the vent path 408 and push the flushing fluid from the flushing chamber 600 through the vent path 408 (e.g., the flushing path 602) into the reaction chamber 208. Stated another way, movement of the second plunger 202 relative to the body 102 and the barrel 104 seals the vent path 408. Continued movement of the second plunger 202 pushes flushing fluid from the flushing chamber 600 along a flushing path 602 formed by a portion of the vent path 408 into the reaction chamber 208. The reagent preparation and dispensing device 100 thereby uses the features and elements defining the vent path 408 for dispensing of the reagent mixture 400 from the dispensing tip 206.

Figure 10:
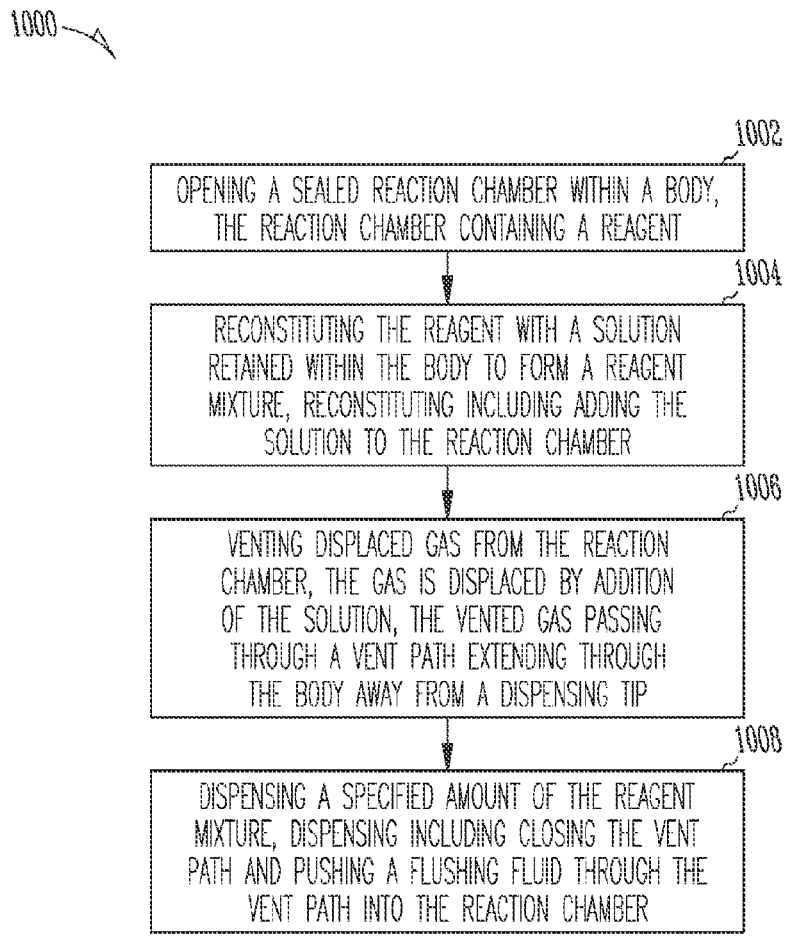
FIG. 10 is a block diagram showing one example of a method for using a reagent preparation and dispensing device.

FIG. 10 shows another example of a method 1000 for using a reagent preparation and dispensing device, such as the device 100 shown in FIGS. 1 through 8F. Reference is made to elements and features described herein using the corresponding numbers previously described. Reference to any particular feature or element is not limiting and instead includes any similar elements described herein as well as their equivalents.

At 1002, a sealed reaction chamber such as the reaction chamber 208 is opened within a body 102 including, for instance, a dispensing tip 206. The reaction chamber 208 includes a reagent 204, such as a lyophilized reagent capable of reconstitution through the addition of a solution. In one example, opening the sealed reaction chamber 208 includes moving a barrel 104 relative to the body 102. The barrel 104, in one example, includes a piercing surface 236. Movement of the barrel forces the piercing surface 236 through a reservoir seal 226 and facilitates communication from the reaction chamber 208 to a solution reservoir 214 containing a solution 212. In another example, the barrel 104 is rotated relative to the body 102 to move the barrel 104 through the reservoir seal 226 to open the reaction chamber 208.

At 1004, the reagent 204 is reconstituted with a solution 212 retained within the body (e.g., the barrel 104 contained within the body) to form a reagent mixture 400. In one example, reconstituting the reagent 204 includes adding the solution 212 to the reaction chamber 208. In one example, the solution 212 is added to the reaction chamber 208 through longitudinal movement of the activator 106 selectively engaged with the first plunger 200 (see FIGS. 3A, 4A). Longitudinal movement of the activator 106 correspondingly moves the first plunger 200 and forces the solution 212 out of the barrel 104 and into the reaction chamber 208 to form the reagent mixture 400. In one example, movement of the barrel 104 relative to the body 102 fills the reagent reservoir 212 leaving the reaction chamber 208 (optionally a portion of the reagent reservoir 210). The addition of the solution 212 is thereby limited to the reaction chamber 208 to localize the solution 212 to the area of the reagent reservoir 210 having the reagent 204.

At 1006, gases in the reaction chamber 208 are vented from the reaction chamber, for instance, along a vent path 408 formed within the reagent preparation and dispensing device 100. The reaction chamber gas is displaced by the addition of the solution 212 to the reaction chamber 208. The vented gas passes through the vent path 408 extending through the body 102 away from the dispensing tip 206. In one example, the body 102 includes the barrel 104. As previously described above and shown in FIGS. 4A and 4B, the vent path 408 in another example extends from the reaction chamber 208 through the reaction chamber vents 410 formed in the dispensing tip 206. A first portion of the vent path 408 extends along an exterior of the barrel 104 toward barrel passages 412 extending through the barrel 104. A second portion of the vent path 408 continues through the barrel 104 along a barrel inner wall (e.g., a vent wall) and the first plunger 200. The second portion of the vent path 408 continues along the second plunger 202 through the barrel 104. As shown in FIG. 4B, in one example, the vent path 408 extends around activator lugs engaged with corresponding barrel stops 406 formed in the barrel 104. The vent path 408 continues out of the barrel 104 to allow venting of the reaction chamber gases to the exterior of the reagent preparation and dispensing device 100. Venting of the reaction chamber gases substantially prevents pressurization of the reaction chamber 208 during reconstitution of the reagent 204. Further, preventing pressurization within the reaction chamber 208 facilitates the addition of the solution 212 to the reaction chamber 208 by substantially eliminating resistance otherwise provided by over pressurization within the reaction chamber 208.

At 1008, a specified amount of the reagent 400 is dispensed from the reagent preparation and dispensing device 100. Dispensing, in one example, includes closing the vent path 408 and pushing a flushing fluid, such as air, through the vent path 408 (e.g., the flushing path 602) into the reaction chamber 208. That is to say, once the vent path 408 is closed, such as by engagement of the second plunger 202 with an interior barrel inner wall 604 of the barrel 104, flushing fluid from a flushing chamber 600 is pushed along a flushing path 602 into the reaction chamber 208. The flushing path 602 utilizes a part of the second portion of the vent path 408 as well as the first portion of the vent path 4008 extending from the barrel passages 412 to the reaction chamber vents 410. That is to say, the method 1000 includes forcing a flushing fluid from the flushing chamber 600 into the reaction chamber 208 to dispense the specified amount of the reagent mixture 400 from the device 100 (see FIG. 7).

In one example, venting gas includes venting gas through the body 102 in a direction opposed to the direction of dispensing the specified amount of the reagent mixture 400. For instance, venting of the reaction gas through the vent path 408 is conducted vertically through the device 100 in a first direction toward the activator 106. The dispensing of the reagent mixture 400 is performed in second opposed direction away from the body 102. By venting the reaction chamber gases in an opposed direction the reagent preparation and dispensing device 100 is maintained in a single vertical orientation as shown through FIG. 8A through 8F during the reconstitution and dispensing steps.

In another example, reconstituting of the reagent 204 is conducted adjacent to the dispensing tip 206 in a first portion of the reaction chamber 208. The reaction chamber gases are vented from a second portion of the reaction chamber remote from the first portion of the reaction chamber. That is to say, the reconstitution of the reagent 208 is conducted at a bottom portion of the reaction chamber 208 and the venting of the displaced reaction chamber gases begins at a second portion of the reaction chamber opposed to the bottom portion of the reaction chamber.

In another example, dispensing the specified amount of the reagent mixture 400 includes moving a plunger such as the second plunger 202 relative to the body 102. Movement of the second plunger 202 closes the vent path 408 by engaging the plunger 202 with a vent wall (e.g., the barrel inner wall 604) to seal a flushing chamber 600 formed by the plunger 202 and the vent wall. Pushing of the flushing fluid from the flushing chamber 600 through the vent path includes moving the plunger 202 through the flushing chamber 600.

In still another example, the method 1000 includes removing a frangible portion of the dispensing tip such as a frangible tip 238. Removal of the frangible tip opens the dispensing tip 206 and provides an open orifice for dispensing of the reagent mixture 400 according to movement of the actuator 106 and the second plunger 202.

CONCLUSION

The reagent preparation and dispensing device shown herein including the methods for making and using the same provide a consolidated device capable of separately retaining a reagent and a solution where the reagent is configured for reconstitution through addition of the solution. The reagent preparation and dispensing device isolates the reagent to substantially prevent the ingress of moisture and thereby preserves the reagent until reconstitution is desired and performed through operation of the device. When operated the reagent preparation and dispensing device is actuated through movement of activator and one or more plungers. The activator and plungers are selectively engaged to prevent movement of the activator relative to one or more of the plungers, the device body and a barrel moveably coupled with the body. By selectively engaging the activator with one or more of the plungers, the body and the barrel staged operation of the reagent preparation and dispensing device is performed. That is to say, each step of the reconstitution and dispensing process is performed by one or more movements of the activator, the barrel, the plunger and the like. As each step of the reconstitution and dispensing process is performed the technician receives affirmative physical feedback from the device indicating completion of the immediate step and readiness of the reagent preparation and dispensing device for the next step of reconstitution and dispensing. By providing staged operation of the reagent preparation and dispensing device the technician is ensured the reagent is fully reconstituted and the specified amount of the reagent is fully dispensed from the device.

As shown herein, the reagent preparation and dispensing device includes one or more vent paths extending from the reaction chamber containing the reagent and containing the reagent mixture after addition of the solution to the reagent. The vent path vents gases from the reaction chamber displaced by the addition of the solution and substantially prevents the development of overpressure within the reaction chamber during reconstitution. By minimizing the development of the pressure within the reaction chamber the technician is able to easily reconstitute the reagent through the addition of the solution without resistance to movement of the activator through back pressure developed within the reaction chamber. Further, by venting reaction chamber gases from the reaction chamber over pressure developed within the reaction chamber is thereby avoided to substantially prevent the risk of premature opening of a dispensing tip or the braking of a seal of the reaction chamber. The reagent is thereby fully reconstituted prior to dispensing of the reagent from the device.

In another example, the vent path allows the reagent preparation and dispensing device to remain in a single upright orientation throughout the reconstitution and dispensing process. Because the vent path extends away from the dispensing tip the reaction chamber gases are vented in a direction opposed to the direction of dispensing thereby allowing the dispensing tip to remain closed throughout the reconstitution process. That is to say, because the dispensing tip and the reaction chamber are sealed (except for the vent path) reconstitution of the reagent is performed in the same orientation used to both breach the seal between the reagent and the solution reservoirs and dispense the reagent mixture. The technician is thereby able to easily reconstitute and dispense the reagent mixture from the device without considering changing the orientation of the device to ensure pressures are not developed within the reaction chamber and the dispensing tip.

Further, in other examples, the reagent preparation and dispensing device includes a flushing chamber sized and shaped to ensure full dispensing of the reagent mixture from the device. As previously described, the flushing chamber, in one example, uses a chamber with flushing fluid having a larger volume relative to the smaller volume of the reaction chamber. Movement of the large volume of flushing fluid through the smaller reaction chamber ensures the specified amount of the reagent mixture is fully flushed from the reaction chamber through the dispensing tip of the device. Residual reagent mixture is thereby cleaned from the reaction chamber and fully dispensed from the reagent preparation and dispensing device. In the example where the reagent preparation and dispensing device includes the flushing chamber the use of a plunger physically engaged with the reagent mixture to dispense the mixture from the device is not needed. Stated another way, because the flushing chamber of the device described in an example herein has a larger volume than the reaction chamber the device is not limited to the displacement caused by a plunger physically engaged with the reagent mixture (e.g., in other words a 1:1 ratio of displacement by the plunger relative to a corresponding volume of a reagent mixture dispensed from the reservoir).

In another example, the reagent preparation and dispensing device with the flushing chamber uses a portion of the vent path as a flushing path to transmit the flushing fluid from the flushing chamber into the reaction chamber for dispensing of the reagent mixture. That is to say, the vent path is a two-way passage allowing the venting of the reaction chamber gases from the reaction chamber in an opening configuration. And in a closed configuration, the vent path allows the transmission of flushing fluid in an opposite direction into the reaction chamber to force the reagent mixture from the reaction chamber out of the device. In still another example, the reagent preparation and dispensing device as described herein use a plunger physically engaged with reagent mixture to dispense the reagent mixture from the device without needing a flushing fluid chamber.

Although the present disclosure has been described in reference to preferred embodiments, persons skilled in the art will recognize that changes may be made in form and detail without departing from the spirit and scope of the present disclosure. It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the present disclosure should, therefore, be determined with reference to the appended claims, along with the full scope of equivalents to which such claims are entitled.

What is claimed is:
1. An apparatus comprising:
 a body including:
  a reaction chamber configured to include a reagent, and
  a solution reservoir configured to include a solution, the solution reservoir is isolated from the reaction chamber;
 a dispensing path extending from the reaction chamber;

an activator movably coupled with the body, the activator includes a mixing configuration and a dispensing configuration, wherein:
in the mixing configuration, the activator is movable to mix the solution with the reagent in the reaction chamber, and
in the dispensing configuration the activator is movable to dispense the solution through the dispensing path; and
a vent path different from the dispensing path extending from a reaction chamber, wherein the vent path vents the reaction chamber gas displaced by the addition of the solution to the reaction chamber throughout movement of the activator from the mixing configuration to the dispensing configuration.

2. The apparatus of claim 1, wherein the dispensing path is configured to be selectably closed.

3. The apparatus of claim 1, wherein the vent path includes a semi-permeable medium that prevents passage of the reagent mixture.

4. The apparatus of claim 1, further comprising a plunger movably coupled with the activator, wherein the plunger is movable to mix the solution with the reagent in the reaction chamber.

5. The apparatus of claim 1, further comprising a barrel movably coupled with the body, and the plunger is movably coupled with the barrel.

6. The apparatus of claim 5, wherein the vent path is isolated from the solution reservoir and in communication with the reaction chamber through a reaction chamber vent.

7. The apparatus of claim 5, wherein the vent path extends through the barrel and along the plunger.

8. The apparatus of claim 7, wherein the vent path extends along a barrel exterior through a first vent portion, and the vent path extends along a barrel interior through a second vent portion.

9. An apparatus comprising:
a body including:
a reaction chamber configured to include a reagent, and
a solution reservoir configured to include a solution, the solution reservoir is isolated from the reaction chamber;
a plunger movably coupled between a starting position and a seated position, wherein:
in the starting position, the solution reservoir and the reaction chamber are isolated, and
in the seated position, the plunger is configured to push the solution into the reaction chamber;
a flushing chamber, different from the reaction chamber, including a flushing fluid in communication with the reaction chamber;
a dispensing path extending from the reaction chamber and out of the body, wherein:
in a closed configuration, the dispensing path is sealed, and
in a dispensing configuration, the dispensing path is configured to deliver a reagent mixture formed from the solution and the reagent; and
a flushing path including the flushing chamber at a first end and the reaction chamber at a second end, wherein the flushing fluid is pushed through the flushing path, and the flushing fluid pushes the reagent mixture from the reaction chamber through the dispensing path.

10. The apparatus of claim 9, further comprising a barrel movably coupled with the body, and the plunger is movably coupled with the barrel.

11. The apparatus of claim 10, wherein the barrel includes a storage configuration and a mixing configuration, including:
in the storage configuration, the solution reservoir is isolated from the reaction chamber and the reaction chamber has a first volume, and
in the mixing configuration, the solution reservoir is in communication with the reaction chamber, the reaction chamber has a second volume smaller than the first volume.

12. The apparatus of claim 11, wherein the barrel translates from the storage configuration to the mixing configuration, and in the mixing configuration, the barrel is received within the reaction chamber.

13. The apparatus of claim 9, further comprising a vent path extending from the reaction chamber, the vent path includes open and closed configurations:
in the open configuration, the vent path extend outside of the body, and the vent path vents reaction chamber gas displaced by the addition of the solution to the reaction chamber, and
in the closed configuration, the vent path is closed, and flushing fluid delivered from the flushing chamber dispenses the reagent mixture through the dispensing path.

14. The apparatus of claim 9, wherein the volume of the flushing chamber is greater than the volume of the reaction chamber.

15. A method of making a vented reconstitution assembly comprising:
coupling a solution reservoir with a body, the solution reservoir configured to store a solution;
coupling a reaction chamber with the body, the reaction chamber configured to store a reagent;
forming a dispensing path from the reaction chamber;
forming a vent path from the reaction chamber, the vent path different from the dispensing path; and
movably coupling an activator with the body, the activator movable in mixing and dispensing configurations, wherein:
in the mixing configuration the activator is movable to mix the solution with the reagent in the reaction chamber, and gas within the reaction chamber displaced by the mixing is vented through the vent path, and;
in the dispensing configuration the activator is movable to dispense the solution through the dispensing path.

16. The method of claim 15, wherein movably coupling the activator with the body includes movably coupling a plunger with the body.

17. The method of claim 15, further comprising movably coupling a barrel with the body.

18. The method of claim 17, wherein movably coupling the barrel includes forming the barrel with a storage configuration and a mixing configuration, including:
in the storage configuration, isolating the solution reservoir from the reaction chamber and the reaction chamber to has a first volume, and
in the mixing configuration, forming the solution reservoir to be in communication with the reaction chamber, wherein the reaction chamber has a second volume smaller than the first volume.

19. The method of claim 17, wherein forming the vent path includes forming the vent path between the barrel and the body.

20. The method of claim 17, wherein forming the vent path includes locating the vent path along a barrel exterior through a first vent portion, and locating the vent path along a barrel interior through a second vent portion.

21. The method of claim 15, further comprising forming a closed dispensing tip along the dispensing path, the dispensing tip including a frangible dispensing tip.

22. The method of claim 21, wherein forming the closed dispensing tip includes forming the closed dispensing tip from a first portion of the reaction chamber, and forming the vent path includes extending the vent path from a second portion of the reaction chamber opposed to the first portion.

23. The method of claim 15, further comprising movably coupling a second plunger with the body, and the second plunger is operable to close the vent path and push a flushing fluid through the vent path into the reaction chamber.

24. The method of claim 15, further comprising forming the volume of the flushing chamber, wherein the volume of the flushing chamber is greater volume than the volume of the reaction chamber.

25. A method of reagent preparation and dispensing comprising:
   maintaining the orientation of a body;
   opening a sealed reaction chamber to a solution reservoir within the body, the reaction chamber containing a reagent;
   reconstituting the reagent with a solution retained within the solution reservoir to form a reagent mixture while maintaining the orientation of the body, reconstituting including adding the solution to the reaction chamber;
   venting displaced gas from the reaction chamber while maintaining the orientation of the body, the gas is displaced by addition of the solution, the vented gas passing through a vent path extending through the body away from a dispensing tip; and
   dispensing a specified amount of the reagent mixture, dispensing including closing the vent path and pushing a flushing fluid through the vent path into the reaction chamber.

26. The method of claim 25, wherein venting displaced gas includes preventing pressurization within the reaction chamber during reconstitution.

27. The method of claim 25, wherein dispensing the specified amount of the reagent mixture includes pressurizing the reaction chamber.

28. The method of claim 25, wherein venting displaced gas includes venting gas through the body in a direction opposed to a direction of dispensing the specified amount of the reagent mixture.

29. The method of claim 25, wherein reconstituting of the reagent is adjacent to the dispensing tip in a first portion of the reaction chamber, and the gas is vented from a second portion of the reaction chamber remote from the first portion.

30. The method of claim 25, wherein dispensing the specified amount of the reagent mixture includes moving a plunger relative to the body, and closing the vent path includes engaging the plunger with a vent wall to seal a flushing chamber formed by the plunger and the vent wall, and pushing the flushing fluid through the vent path includes moving the plunger through the flushing chamber.

31. The method of claim 25, further comprising maintaining the orientation of the body that includes positioning the dispensing tip in a downward direction.

32. The method of claim 25, further comprising flushing the reagent mixture from the reaction chamber, wherein a flushing fluid is pushed from a flushing chamber through a flushing path to flush the reagent mixture from the reaction chamber through the dispensing path.

33. The method of claim 32, further comprising pushing the flushing fluid from the flushing chamber through the flushing path, wherein the volume of the flushing fluid is greater than the volume of the reaction chamber.

34. The method of claim 25, further comprising translating a barrel from a storage configuration to a mixing configuration, wherein:
   in the storage configuration, the solution reservoir is isolated from the reaction chamber and the reaction chamber has a first volume, and
   in the mixing configuration, the solution reservoir is in communication with the reaction chamber, the reaction chamber has a second volume smaller than the first volume.

* * * * *